US009261495B2

(12) United States Patent
Krockenberger et al.

(10) Patent No.: US 9,261,495 B2
(45) Date of Patent: Feb. 16, 2016

(54) METHOD FOR FLAGGING A BLOOD SAMPLE

(71) Applicant: Abbott Laboratories, Abbott Park, IL (US)

(72) Inventors: Martin Krockenberger, Los Gatos, CA (US); Richard Bordenkircher, Meridian, ID (US); Diana Garrett, Scotts Valley, CA (US); John Glazier, San Jose, CA (US); James Bearden, Milpitas, CA (US); Bodo Roemer, Saulheim (DE); Giacomo Vacca, San Jose, CA (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 14/562,046

(22) Filed: Dec. 5, 2014

(65) Prior Publication Data

US 2015/0160188 A1 Jun. 11, 2015

Related U.S. Application Data

(63) Continuation of application No. 12/546,552, filed on Aug. 24, 2009, now Pat. No. 8,911,669.

(51) Int. Cl.
*G01N 33/00* (2006.01)
*G01N 31/00* (2006.01)
(Continued)

(52) U.S. Cl.
CPC ........ *G01N 33/4915* (2013.01); *G01N 15/1459* (2013.01); *G01N 33/492* (2013.01);
(Continued)

(58) Field of Classification Search
CPC .................. G01N 15/1459; G01N 2015/1486; G01N 15/1434; G01N 15/0205; G01N 15/0227; G01N 15/1463; G01N 2015/025; G01N 2015/1452; G01N 2015/1493; G01N 15/1425; G01N 1/38; G01N 2015/0065; G01N 2015/1006; G01N 2015/1402; G01N 2015/1447; G01N 2015/1488; G01N 2015/1477; G01N 15/147; G01N 2015/0073; G01N 2015/008; G01N 2021/0346; G01N 2021/6493; G01N 21/6428; G01N 21/645; G01N 15/00; G01N 2015/0069; G01N 2015/0076; G01N 2015/0084; G01N 33/49; G01N 33/4915
USPC .................................. 422/50, 73, 400; 436/10
See application file for complete search history.

(56) References Cited

U.S. PATENT DOCUMENTS

| 4,882,284 A | 11/1989 | Kirchanski et al. |
| 5,017,497 A | 5/1991 | Gerard de Grooth et al. |

(Continued)

FOREIGN PATENT DOCUMENTS

WO          WO 93/16384          8/1993

OTHER PUBLICATIONS

Begemann et al. (1989) Atlas of Clinical Hematology, 4th Edition, pp. 227-230, Springer-Verlag.

(Continued)

*Primary Examiner* — Dean Kwak
(74) *Attorney, Agent, or Firm* — Edward J. Baba; Bozicevic, Field & Francis LLP

(57) ABSTRACT

A hematology analyzer is provided. In certain embodiments, the hematology analyzer comprises: a) a flow cell; b) a light source for directing light to the flow cell; c) a plurality of detectors for detecting a plurality of optical characteristics of a blood cell passing through the flow cell; and d) a data analysis workstation programmed to: i. enumerate test blood cells passing through the flow cell; and ii. flag a blood sample as containing lysis-resistant red blood cells or fragile white blood cells.

20 Claims, 14 Drawing Sheets

(51) Int. Cl.
  *G01N 33/49* (2006.01)
  *G01N 15/14* (2006.01)
  *G01N 15/00* (2006.01)
  *G01N 15/10* (2006.01)

(52) U.S. Cl.
  CPC .. *G01N2015/008* (2013.01); *G01N 2015/0069* (2013.01); *G01N 2015/1006* (2013.01); *G01N 2015/1486* (2013.01); *G01N 2015/1488* (2013.01); *Y10T 436/101666* (2015.01); *Y10T 436/2575* (2015.01)

(56) References Cited

U.S. PATENT DOCUMENTS

| | | |
|---|---|---|
| 5,266,269 A | 11/1993 | Niiyama et al. |
| 5,378,633 A | 1/1995 | Von Behrens et al. |
| 5,631,165 A | 5/1997 | Chupp et al. |
| 6,524,858 B1 | 2/2003 | Zelmanovic et al. |
| 6,549,876 B1 | 4/2003 | Yundt-Pacheco |
| 2008/0153170 A1 | 6/2008 | Garrett et al. |
| 2008/0158561 A1 | 7/2008 | Vacca et al. |
| 2008/0268494 A1 | 10/2008 | Linssen |

OTHER PUBLICATIONS

Bremmelgaard and Nygard (1991) Interference by cryoglobulins with white blood cell measurements on Coulter Counter, *Scand. J. Clin. Lab. Invest.* 51(5):489-492.

Clinical and Laboratory Standards Institute (2007) "Reference Leukocyte (WBC) Differential Count (Proportional) and Evaluation of Instrumental Methods: Approved Standard" Second Edition, H20-A2 27(4):1-63.

Cross and Strange (1987) "Erroneous Ortho ELT800/WS WBC in chronic lymphatic leukaemia" *Clin. Lab. Haemat.* 9(4):371-376.

Densmore (1981) "Eliminating Disintegrated Cells on Hematologic Films" *Laboratory Medicine* 12:640-641.

Dixon et al. (1981) "Electronic counting of dog leucocytes. Discrepancies arising from calibration with Coulter standard 4C and with the haemocytometer" *Research in Veterinary Science* 31(2):249-252.

England et al. (1982) "An assessment of the Ortho ELT-8" *Clin. Lab. Haemat.* 4(2):187-199.

The PCT Invitation to Pay Additional Fees, PCT/US2010/046082, Date of Mailing Dec. 23, 2010.

International Search Report for Application No. PCT/US2010/046082, Date of Mailing Aug. 19, 2011.

METHOD FOR FLAGGING A BLOOD SAMPLE

BACKGROUND OF THE INVENTION

Flow cytometry is a technique for counting, examining, and sorting microscopic particles suspended in a stream of fluid. Flow cytometry allows simultaneous, multiparametric analysis of the physical and/or biochemical characteristics of single cells flowing through an optical/electronic detection apparatus. When used in a hematology analyzer, flow cytometry enables the precise counting of cells in a measured volume of blood or other biological fluid sample and the identification of those cells based on the use of light scattering and/or fluorescence detection.

This disclosure relates in part to a hematology analyzer, and a method for flagging a blood sample as containing lysis-resistant red blood cells or fragile white blood cells.

SUMMARY OF THE INVENTION

A hematology analyzer is provided. In certain embodiments, the hematology analyzer comprises: a) a flow cell; b) a light source for directing light to the flow cell; c) a plurality of detectors for detecting a plurality of optical characteristics of a blood cell passing through the flow cell; and d) a data analysis workstation programmed to: i. enumerate test blood cells passing through the flow cell; and ii. flag a blood sample as containing lysis-resistant red blood cells or fragile white blood cells. The flagging can be done by analyzing data for the test blood cells to produce a value that describes a characteristic of the test blood cells; comparing the value to a criterion obtained from analysis of a plurality of reference samples comprising blood cells; and flagging the blood sample as containing lysis-resistant red blood cells or fragile white blood cells if the value meets the criterion.

DETAILED DESCRIPTION

Figure 1:
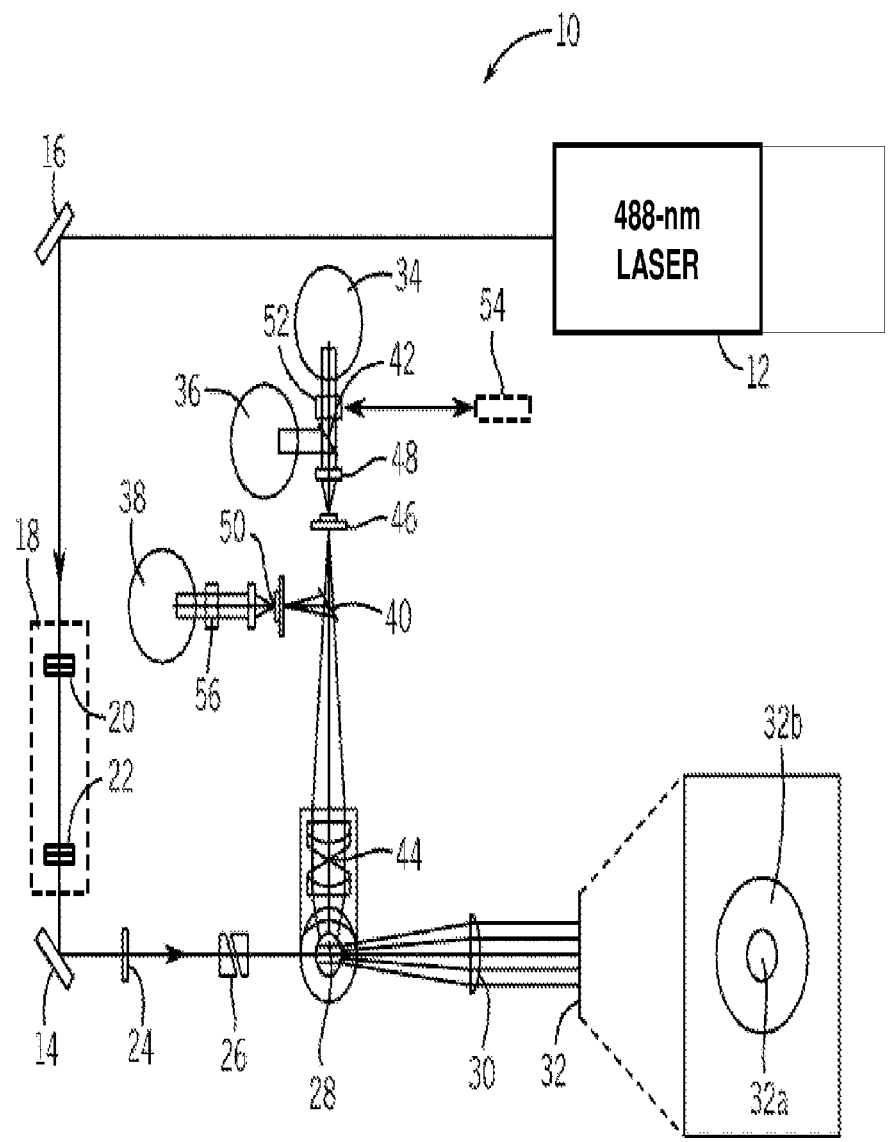
FIG. 1 is a schematic illustration of the optical subassembly of an exemplary hematology analyzer.

Before the present invention is described in detail, it is to be understood that this invention is not limited to particular variations set forth and may, of course, vary. Various changes may be made to the invention described and equivalents may be substituted without departing from the true spirit and scope of the invention. In addition, many modifications can be made to adapt a particular situation, material, composition of matter, process, process act(s) or step(s), to the objective(s), spirit or scope of the present invention. All such modifications are intended to be within the scope of the claims made herein.

Steps of any method recited herein can be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described can be set forth and claimed independently, or in combination with any one or more of the features described herein.

The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. For example, if a value is compared to "a criterion", the value may be compared to one or more criteria, i.e., a single criterion or multiple criteria. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

The following abbreviations are used in this disclosure: RBC (red blood cell or erythrocyte), rRBC (lysis-resistant red blood cell or erythrocyte), WBC (white blood cell or leukocyte), fWBC (fragile white blood cell or leukocyte), DSS (depolarized side scatter), CLL (chronic lymphocytic leukemia), ALL (axial light loss), IAS (intermediate angle scatter), PSS (polarized side scatter) and DSS (depolarized side scatter), NEU (neutrophils), LYM (lymphocytes), MON (monocytes), MCV (mean cell volume), RDW (red blood cell distribution width), PLT (platelet), CBC (completed blood count), HGB (hemoglobin), and FCS (flow cytometry standard).

In this disclosure, we use the term "FCS file" to describe a digital representation of the collection of detected events captured by the analyzer and classified (as, e.g., RBCs, lymphocytes, etc.) by automated internal algorithms. The events in the FCS file may also be referred to as "list mode" data, reflecting one aspect of the FCS file format, in which events are arranged in a list ordered sequentially by time of detection.

Hematology Analyzers

As noted above, a hematology analyzer that is capable of: a) enumerating test blood cells and b) flagging a blood sample as containing lysis-resistant red blood cells (rRBCs) or fragile white blood cells (fWBCs) is provided. The sample may be flagged as containing rRBCs or fWBCs by: analyzing data for a test sample to produce a value that describes a characteristic of blood cells in the test sample; comparing the value to a criterion obtained from analysis of a plurality of reference samples comprising blood cells; and flagging the blood sample as containing lysis-resistant red blood cells or fragile white blood cells if the value meets the criterion.

The methodology described below may be generally employed on any suitable flow cytometer, including a hematology analyzer, examples of which are known on the art and described in, e.g., U.S. Pat. Nos. 5,378,633, 5,631,165, 6,524, 858, 5,266,269, 5,017,497 and 6,549,876, as well as published U.S. Patent Applications US20080153170, US20080158561 and US20080268494, the disclosures of which are incorporated herein by reference in their entirety. Hematology analyzers analyze samples of whole blood to determine, among other results, the concentration of total white blood cells and the concentrations of white blood cell sub-populations, which include, but are not limited to, neutrophils, lymphocytes, monocytes, eosinophils, and basophils. The optical subassembly of an exemplary hematology analyzer is schematically illustrated in FIG. 1. One of skill in the art would recognize that the choice, number and design of the components (e.g., the type of laser used, the number and specifications of the optical components, etc.) can vary greatly between analyzers and, as such, the hematology analyzer of FIG. 1 is provided as an example and should not be used to limit this disclosure. For example, in certain cases a hematology analyzer may or may not detect fluorescence.

Referring now to FIG. 1, exemplary hematology analyzer 10 comprises a source of light 12, a front mirror 14 and a rear mirror 16 for beam bending, a beam expander module 18 containing a first cylindrical lens 20 and a second cylindrical lens 22, a focusing lens 24, a fine beam adjuster 26, a flow cell 28, a forward scatter lens 30, a bull's-eye detector 32, a first photomultiplier tube 34, a second photomultiplier tube 36, and a third photomultiplier tube 38. The bullseye detector 32 has an inner detector 32a for measuring extinction of the forward-propagating beam (the data produced therefrom being referred to as "axial light loss" or "ALL") and an outer detector 32b for light scattering in an annulus of 3° to 10° from forward (otherwise referred to as "intermediate angle scatter" or "IAS"). The source of light 12 can be a vertically polarized 488-nm air-cooled argon-ion laser or a vertically polarized blue (488 nm) solid-state laser. Additional details relating to the laser, the flow cell, the lenses, the focusing lens, the fine-beam adjust mechanism and the laser focusing lens can be found in U.S. Pat. No. 5,631,165, incorporated herein by reference, particularly at column 41, line 32 through column 43, line 11.

The forward optical path system of the hematology analyzer shown in FIG. 1 includes a spherical plano-convex lens 30 and a two-element photo-diode detector 32 located in the back focal plane of the lens. In this configuration, each concentric ring within the outer photodiode detector 32b maps to a specific collection angle of light from cells moving through the flow cell 28. The detector 32 can be a bull's-eye detector capable of detecting axial light loss (ALL) and intermediate angle forward scatter (IAS). U.S. Pat. No. 5,631,165 describes various alternatives to this detector at column 43, lines 12-52.

The first photomultiplier tube 34 (PMT1) measures depolarized side scatter (DSS) or green fluorescence (FL1). The second photomultiplier tube 36 (PMT2) measures polarized side scatter (PSS) or yellow to orange fluorescence (FL2) and the third photomultiplier tube 38 (PMTS) measures red fluorescence (FL3). FL1, green fluorescence, is detected between about 515 to 545 nm FL2, yellow to orange fluorescence, is detected between about 565 to 595 nm FL3, red fluorescence, is detected between about 615 to 645 nm. Side-scatter and fluorescent emissions are directed to these photomultiplier tubes by dichroic beam splitters 40 and 42, which transmit and reflect efficiently at the required wavelengths to enable efficient detection. U.S. Pat. No. 5,631,165 describes various additional details relating to the photomultiplier tubes at column 43, line 53 though column 44, line 4.

Sensitivity is enhanced at photomultiplier tubes 34, 36, and 38, when measuring fluorescence, by using an immersion collection system. The immersion collection system is one that optically couples the first lens of condenser assembly 44 to the flow cell 28 by means of a refractive index-matching layer, enabling collection of light over a wide angle. U.S. Pat. No. 5,631,165 describes various additional details of this optical system at column 44, lines 5-31.

The condenser 44 is an optical lens system with aberration correction sufficient for diffraction-limited imaging used in high resolution microscopy. U.S. Pat. No. 5,631,165 describes various additional details of this optical system at column 44, lines 32-60.

The functions of other components shown in FIG. 1, i.e., a slit 46, a field lens 48, and a second slit 50, are described in U.S. Pat. No. 5,631,165, at column 44, line 63 through column 45, line 15. The photomultiplier tubes 34, 36, and 38 detect either side-scatter (light scattered in a cone whose axis is approximately perpendicular to the incident laser beam) or fluorescence (light emitted from the cells at a different wavelength from that of the incident laser beam). A slider assembly placed in front of photomultiplier 34 allows dual use of photomultiplier 34: to detect depolarized side scatter (DSS) when polarizer 52 is moved in the light path, and to detect green fluorescence (FL1) when filter 54 is moved in the light path. A similar slider assembly (not shown) placed in front of photomultiplier 36 allows the dual use of detecting polarized side scatter (PSS) and yellow-orange fluorescence (FL2). Photomultiplier 38 is configured with filter 56 to detect red fluorescence (FL3) only.

As would be readily apparent, numerous variations of the above-described analyzer are possible. For example, the two cylindrical two lenses may be replaced by an anamorphic prism pair, the bull's-eye detector can be replaced by separate detectors and a holed mirror, and other wavelengths of light may be employed.

An example of a hematology analyzer that does not detect fluorescence is described in U.S. Pat. No. 5,378,633, particularly at col. 24, line 47 to col. 25, line 36 and FIGS. 6 and 7. This description is incorporated by reference herein.

The measurement process begins as the cell stream passes through the flow cell 28, having been diluted with the lysing agent so that the cells pass through the laser-illuminated volume substantially in single file, in a laminar flowing sample stream surrounded by a sheath fluid. The illuminated volume is bounded by the intersection of the laser beam and the sample stream, and in one embodiment it has the approximate dimensions of 80 µm along the laser propagation direction, 20 μm along the sample stream flow direction, and about 5-10 μm in a direction transversal to both sample flow and laser beam propagation.

A whole blood sample is treated with an erythrolytic agent in order to lyse the erythrocytes (red blood cells) in the sample and thereby produce a lysed sample of blood. The hematology analyzer then measures the light scattering characteristics of cells in the lysed sample to produce data. The data may be analyzed in order to enumerate the leukocytes in the sample, as well as to enumerate and classify the leukocyte subpopulations (i.e., lymphocytes, neutrophils, eosinophils, basophils and monocytes), as well as to flag a sample as having lysis-resistant red blood cells or fragile white blood cells.

In use, a suspension of blood in which the erythrocytes have been lysed is propelled at low velocity from a sample nozzle where it comes into contact with a fast-moving, laminar-flow sheath stream. In a process known as hydrodynamic focusing, the sample stream is squeezed into a thin central core. This arrangement usually ensures that only a single leukocyte is in the sensing region of the laser beam at any given time.

A lysis-surviving leukocyte that enters the focused laser beam will scatter light in all directions. Since the wavelength of the light is small compared with the cell size, this scattering phenomenon is approximately described by Mie theory. A part of the scattered light is collected by the photodetectors. In one embodiment, two silicon photodiodes measure light scattered at half angles of about 1-3 degrees and about 3-10 degrees with respect to the axis of the laser beam. These photodiodes may be respectively termed the "0 degree" and "10 degree" detectors. Direct laser light is blocked by an obscuration bar. Light scatter at these low angles is a complex function dominated by cell size and average refractive index with some contribution from cell structure or complexity.

Light scattered at 90 degrees to the axis of the laser beam may be collected using photomultipliers (PMTs). Photomultipliers, not photodiodes, are used in the 90-degree channels because relatively little light is scattered at high angles, and because they are also used to detect the generally much lower-intensity fluorescence emissions. If the impinging polarized light undergoes optical scattering mainly from the cell membrane and nucleus (if present), it generally retains its original vertical plane of polarization. However, if it interacts with certain subcellular components that may be present in the cytoplasm, e.g., granules or anisotropic structures, then the scattered light can have an altered angle of polarization. In order to exploit this phenomenon, one of the PMTs may have a horizontal polarizer in front of it. This polarizer prevents vertically polarized light from striking the photomultiplier. Therefore, any light detected by the "90-degree depolarized" PMT is light that has been depolarized by its interaction with a cellular substructure—usually a leukocyte, and particularly a eosinophil. The second photomultiplier (the "90-degree polarized" PMT) may receive the scattered light reflected off a beam splitter that is angled at 45 degrees and designed to mostly reflect vertically polarized light and mostly transmit horizontally polarized light at the excitation (laser) wavelength. The major portion of the light detected by this second photomultiplier is vertically polarized side-scattered light and carries information correlated with the conformation of the nucleus. The scattering light detection scheme briefly summarized here is a proprietary design referred to as Multi-Angle Polarized Scattering Separation (MAPSS), and described in fuller detail in U.S. Pat. No. 5,017,497. This description is incorporated by reference herein.

Data obtained from the photosensors may be used to construct a four-dimensional scattergram. This can be viewed using the computer graphics capabilities of the instrument which enable a three-dimensional "solid" representation to be rotated in space—with the fourth dimension made manifest through selection of different colors for the pixels representing differing pulse magnitudes in that fourth dimension. For purposes of paper documentation, the four-dimensional scattergram can be examined by six user-selectable pairs of two dimensional scatter plots or projections and by numerous user-selectable one-dimensional histogram projections.

Erythrolytic agents that lyse red blood cells but not leukocytes are known and may contain an aqueous solution of an oxyalcohol (to protect leukocytes from lysis), an organic buffer (having pH at or near 8.5, which serves to provide pH buffering capacity and to increase electrical conductivity of the erythrolytic agent), and a surfactant component (which contributes to the lysis of the erythrocytes). The erythrolytic reagent combination should have low osmolarity to increase the effectiveness of the lysis process. The oxyalcohol used may be 2-phenoxyethanol. The organic buffer may be selected from the group consisting of TRIS/HCl, boric acid, glycylglycine and BICENE™. The surfactant can be selected from the group consisting of TRITON X-100™, TRITON X-114™, and polyoxyethylene or saccharide-derived surfactants. In certain embodiments, the erythrolytic agent contains 2-phenoxyethanol at a concentration between 20 mM and 80 mM, TRIS™/HCl buffer and TRITON X-100™.

In a particular embodiment, the erythrolytic agent contains an aqueous solution of TRITON X-100™, 2-phenoxyethanol, and TRIS™/HCl buffer. Whole blood is mixed with an excess (e.g. thirty- to fifty-fold) of this erythrolytic agent. Lysis of the red blood cells occurs extremely rapidly due to the combination of osmotic shock, the action of the surfactant, and the pH of about 8.5. In the optimized formulation, 2-phenoxyethanol is present at a concentration of about 41 mM, although a useful range of concentrations exists between 20 and 80 mM. The pH of the TRIS™ buffer can be decreased to pH 8.1 without significant effects on its performance. If the pH of the buffer is increased above 9.0, the erythrolytic agent becomes more erythrolytic and more rapid lysis will occur. The presence of trace amounts (up to about 5% vol./vol. of TRITON X-100™) or a similar surfactant helps to ensure complete erythrolysis in specimens which are typically regarded as difficult to lyse, but this also accelerates lysis.

Other organic buffers may be substituted for TRIS™/HCl. Among those with pH at or near 8.5 are boric acid, glycylglycine and BICENE™ (available through CalBiochem) which can be used in the erythrolytic agent. TRITON X-114™ can be used as the surfactant component of the erythrolytic agent. Other hydrophilic surfactants can be selected from those having polyoxyethylene or saccharide head groups.

Methodology

Several embodiments of a method that employs data collected from reference samples to flag samples as containing lysis-resistant red blood cells (rRBCs) or fragile white blood cells (fWBCs) are described below. In certain embodiments, this method includes: a) lysing red blood cells in a whole blood sample to produce a lysed sample of blood; b) subjecting the lysed sample of blood to analysis using a hematology analyzer to obtain data for cells in the lysed sample; c) analyzing data to provide a value that describes a characteristic of the cells; d) comparing the value to a criterion obtained from analysis of a plurality of reference samples of lysed blood; and e) flagging the lysed sample of blood as containing lysis-resistant red blood cells or fragile white blood cells if the value meets the criterion. In addition to the above, the hematology analyzer may produce a report indicating that the lysed sample of blood is flagged as containing lysis-resistant red blood cells or fragile white blood cells, if the value meets the criterion. The method may be executed automatically by the hematology analyzer.

As mentioned above and as will be described in greater detail below, a blood sample may be flagged if a value "meets" a criterion. Since some of the methods described below may require comparison of one number (the value) to another number (the criterion) to determine if a criterion is met, a criterion may be met if: a) the value is the same as the criterion, b) the value is greater than the criterion or c) the value is below the criterion, depending on the relationship between the value and the criterion.

Certain parts of this disclosure refer to "test" blood cells, where "test" blood cells are the cells of a blood sample that is being analyzed by a hematology analyzer.

In certain embodiments and as will be described in greater detail below, the data for a test sample is analyzed to provide a value that describes a characteristic of the test sample, and that value is compared to a criterion obtained from a plurality of reference samples. In essence, the value that describes a characteristic of the cells of test sample is evaluated to determine whether it is a statistical outlier relative to the reference samples, where the criterion is a threshold that determines whether or not the value is significantly different to what would be expected if the sample were "normal" in the sense that it does not contain rRBCs or fWBCs.

In particular embodiments, the value is based on a number that describes the characteristic of the sample (e.g., the slope of a line of best fit, distance from two points on a graph, box ratio, width of distribution, skewness, etc.) plus or minus a measure of the variation that would be expected for that number based on a number of prior samples that were previously run on the same machine. In these embodiments, the value used can be the aforementioned number, plus or minus at least one (e.g., at least 2, at least 2.5, at least 3 up to 4, 5 or 6 or more) standard deviations from that number, based on the variation of the prior samples. Likewise, the criterion to which the value is compared can be based on a number that describes the same characteristic of the reference samples (e.g., the slope of a line of best fit, distance from two points on a graph, box ratio, width of distribution, skewness, etc.), plus or minus a measure of the variation of that number in the reference samples. In these embodiments, the criterion used can be a number that describes the same characteristic in the reference samples, plus or minus at least one (e.g., at least 2, at least 2.5, at least 3 up to 4, 5 or 6 or more) standard deviations from that number. Depending on the methodology employed, the criterion can be a static or continuously updated criterion. A static criterion is a criterion that is not continuously updated each time a sample is run on the analyzer, but rather based on data obtained from a plurality of samples (e.g., at least 5, 10, 20, 50, 100, 500, 1,000, 10,000, or 100,000 samples) that were previously run on a different machine. A continuously updated criterion is updated each time a normal sample (i.e., a sample that meets pre-determined criteria for normality) is run on the analyzer, where the criterion is a continuously updated criterion obtained from at least the prior 5, 10, 50, 100, 200, 500, 1,000, or 10,000 samples analyzed by the same hematology analyzer. A static criterion may be described as being "hardwired" into the analyzer and stays constant during the lifetime of the machine, whereas the dynamically updated criterion is continually updated as new samples are run. In certain embodiments, the static criterion may be periodically updated (e.g., as needed every year or every few years) if the static criterion changes, or if a change in the analyzer software or data station software alters the static criterion.

In particular embodiments, the data for a test sample may be first analyzed within the context of data from continuously updated samples (i.e., data from at least the prior 5, 10, 50, 100, 200, 500, 1,000, or 10,000 samples analyzed by the hematology analyzer) to provide a value that indicates how similar a characteristic of the test sample is to that of prior samples analyzed on the same machine. Once that value has been determined, it can be compared to a static criterion to determine if the test sample contains rRBCs or fWBCs. As such, in certain embodiments the value can be obtained by comparing data for the test blood cells to data obtained from a plurality of reference samples that were previously run on the same machine. In certain cases this embodiment can control for machine-to-machine variability, particularly when optical parameters of a sample are evaluated. In other embodiments, the value for a test sample can obtained by analysis of only the data for the test sample (i.e., without the use of data from dynamically updated samples). Once that value has been determined, it can be compared to a criterion—either a dynamically updated criterion or a static criterion—to determine if the test sample contains rRBCs or fWBCs.

In certain cases, the data analysis workstation of the hematology analyzer can contain a memory containing data obtained from a plurality of prior reference samples analyzed by that machine, as well as a criterion. The data analysis workstation can be programmed to update that data continuously as blood samples are analyzed on the analyzer. The hematology analyzer can further be programmed to adjust the data obtained for a cell sample (i.e., adjust the numbers of a particular cell type) in accordance with the analysis described above and below. For example, if rRBCs are identified, then the number of cells identified as leukocytes or lymphocytes can be decreased.

Exemplary cell characteristics and methods for providing a value that describes such cell characteristics are described below.

Cell count decrease

In one embodiment, the characteristic of the cells is the rate of cell count decrease over a period of time. As such, in certain embodiments, the hematology analyzer measures the rate of decrease in a number of cells counted in the test samples of lysed blood over a period of time (typically a few seconds, e.g., at least 2 seconds, at least 5 seconds, at least 10 seconds, at least 20 seconds, or more) by counting the number of cells per unit of time (e.g., at intervals of at least 10 ms, at least 50 ms, at least 100 ms or at least 200 ms, or more) over the period of time. The lysed sample of blood may be flagged if the rate of decrease in the number of cells counted is significantly greater than the rate of decrease in the number of cells counted in the reference samples of lysed blood.

In certain embodiments, temporal data obtained from a sample can be analyzed using standard statistical methods to provide the slope of the line of best fit for the cells, as well as a measure of the variability of the data (e.g., the standard deviation or "sigma" of the data) to the line of best fit. In these embodiments, the value that is compared to the criterion may be the slope of the line of best fit for the test cells, plus at least one standard deviation (e.g., at least 2, at least 2.5, at least 3 up to 4, 5 or 6 or more standard deviations) of the slope of the line of best fit for the cells.

In this embodiment, the criterion to which the value obtained from the test cells is compared can be based on the slope of the lines of best fit for the reference samples, where, in certain cases, the mean slope of the lines of best fit for the reference samples is employed. In particular embodiments, temporal data obtained from a plurality of reference samples can be analyzed to provide a corresponding plurality of lines of best fit for the reference samples. The criterion employed in this embodiment can be based on the mean slope of the lines of best fit for the reference cells, as well as a measure of the variability of the slopes of the lines of best fit (e.g., the standard deviation of the slopes of the lines of best fit). In these embodiments, the criterion to which the value is compared can be the mean slope of the lines of best fit for the reference cells, minus at least one standard deviations (e.g., at least 2, at least 2.5, at least 3 up to 4, 5 or 6 or more standard deviations) of the mean slope of the lines of best fit for the reference cells.

Figure 2:
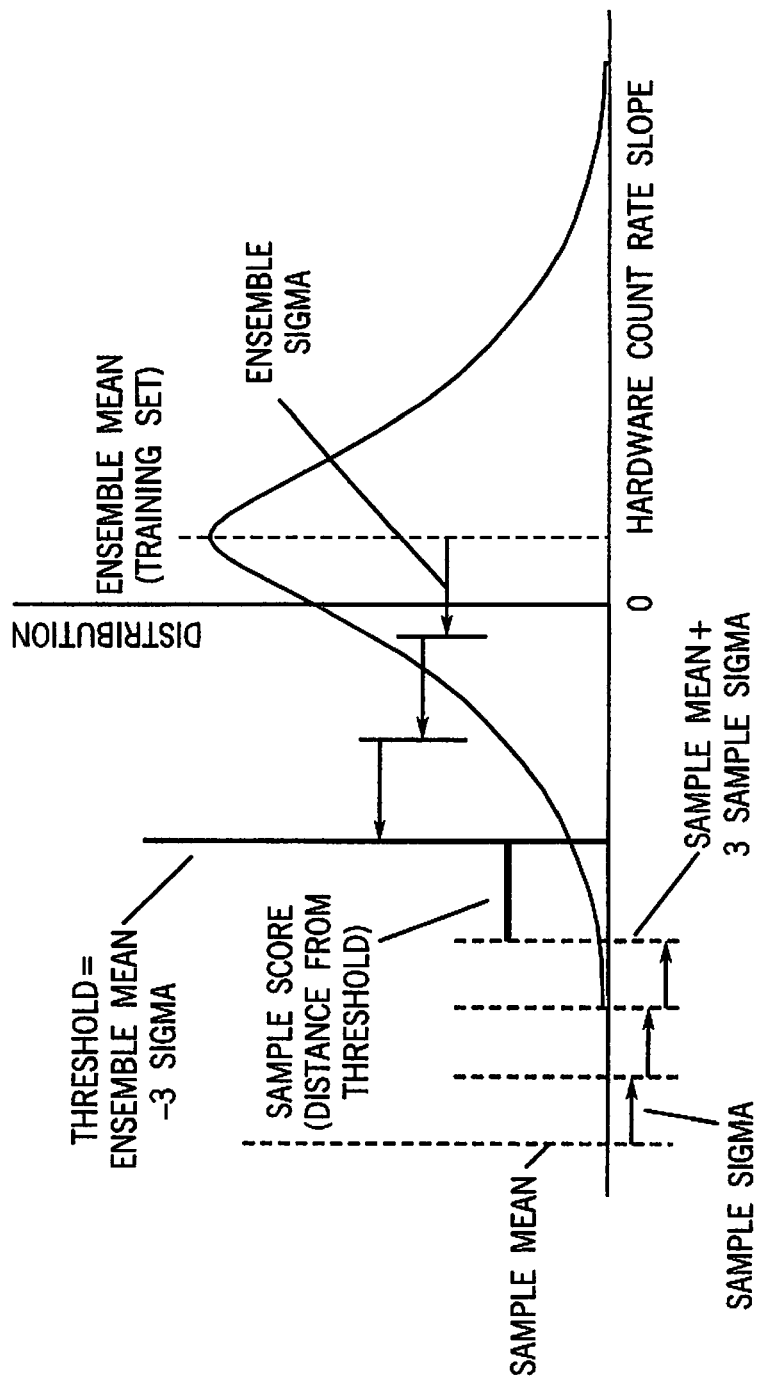
FIG. 2 is a graph showing the use of the total-count slope in flagging a sample.

In one exemplary embodiment illustrated in FIG. 2, the value for the test sample data is the sample's slope of the line of best fit plus three standard deviations, and the criterion is the mean slope of the line of best fit for the reference samples, minus three standard deviations. If the value meets the criterion, the sample may be flagged.

In particular embodiments, if the value meets the criterion a "score" can be provided that indicates the numerical distance between the value and the criterion. In the embodiment shown in FIG. 2, the score does meet the criterion (i.e., is more negative than the criterion), and therefore the sample can be flagged. The more different the value is from the criterion, the higher the score.

In these embodiments, the criterion may be continuously updated or static. However, since the rate of cell count decrease should not vary significantly from machine to machine, the criterion employed in many embodiments can be a static criterion. For example, the criterion shown in the graph of FIG. 3 was calculated using the temporal data for over 2,000 samples run on multiple different machines.

The hematology analyzer measures the rate of decrease in the total number of cells or the number of cell classified as lymphocytes counted in the test samples of lysed blood over a period of time. If the value indicates the rate of decrease in the total number of cells counted in the lysed sample over a period of time, then the lysed sample of blood can be flagged if the rate of decrease for the test sample is significantly greater than the rate of decrease in the total number of cells counted in the reference samples of lysed blood. Likewise, if the value indicates the rate of decrease in the number of cells classified as lymphocytes counted in the lysed sample over a period of time, then the lysed sample of blood may be flagged if the rate of decrease is significantly greater than the rate of decrease in the number of cells classified as lymphocytes counted in the reference samples of lysed blood. In certain cases the method may provide a score indicating the rate of decrease of total cells, and a score indicating the rate of decrease in cells classified as lymphocytes.

In particular embodiments, the temporal data may be further analyzed to determine if the rate of decrease in the number of cells counted (either total cells in the sample, or cells classified as lymphocytes) is increasing or decreasing, where an increasing rate of decrease suggests that the lysed sample of blood contains fragile white blood cells; and a decreasing rate of decrease suggests that the lysed sample of blood contains resistant red blood cells. In these embodiments, a non-linear second-order polynomial analysis can be performed on the data, and the sign of the second-order coefficient of the line of best fit indicates whether the rate of decrease in the number of cells counted is increasing or decreasing. A positive second-order coefficient suggests that the sample contains rRBCs, whereas a negative second-order coefficient suggests that the sample contains fWBCs. As such, in certain embodiments, in addition to flagging a sample as containing rRBCs or fWBCs, the analyzer can also indicate which of those cells a sample contains. In certain cases, because samples containing rRBCs are more common that samples containing fWBCs, a sample may be flagged as likely containing rRBCs rather than fWBCs without performing any second-order polynomial analysis. In such cases, a follow-up assay to identify the interfering substance may be recommended.

Lymphocyte geometric distance

In another embodiment, the data comprises the axial light loss (ALL) and intermediate angle scatter (IAS) values for cells of the test sample that are classified as lymphocytes, the value is based on the mean ALL and mean IAS values for the test cells, and the criterion is based on the median of the means of the ALL and IAS values for the reference cells.

In this embodiment, the analyzer can independently calculate and store the mean ALL and mean IAS values for a plurality of prior samples run on the analyzer (e.g., data from at least the prior 5, 10, 50, 100, 200, 500, 1,000, or 10,000 normal samples analyzed by the hematology analyzer). As a test sample is analyzed, the mean ALL and mean IAS values for cells that are classified as lymphocytes is calculated and the geometric distance (i.e., the Euclidian distance in the two-dimensional ALL-IAS space) is determined between: a) the mean ALL and IAS values for cells that are classified as lymphocytes in the test sample and b) the median of the mean ALL and IAS values for the plurality of prior samples. While the computed distance may itself indicate that the sample may be an "outlier" if it is sufficiently large (thereby suggesting that the test sample contains rRBCs), the computed distance may be compared to a static criterion that is based on the geometric distances (the distance between the mean ALL and mean IAS values for a sample, and the median of the mean ALL and IAS for the reference cells) for cells that are classified as lymphocytes in each of the reference samples plus at least one standard deviation (e.g., at least 2, at least 2.5, at least 3 up to 4, 5 or 6 or more standard deviations) from the mean.

Figure 5:
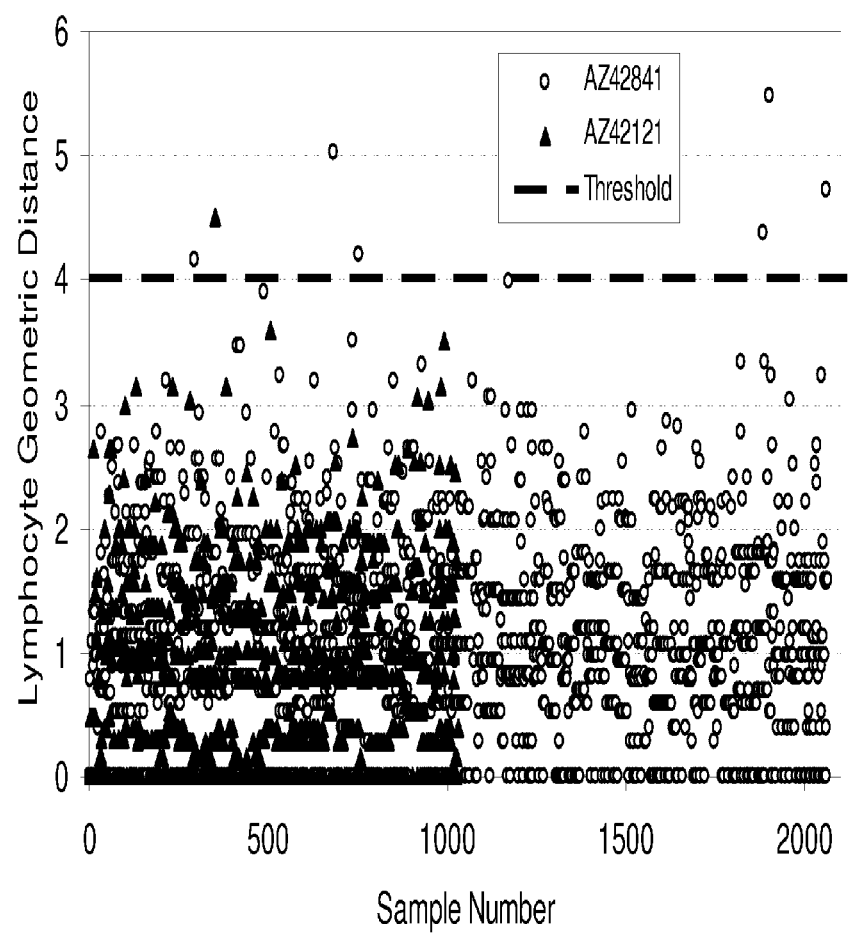
FIG. 5 is a graph showing the distribution of lymphocyte peak distances for a set of normal reference samples and the threshold above which a flagging score is accumulated.

In the example shown in FIG. 5, the static criterion is set at 4.0, which represents the mean geometric distance (1.1) plus approximately 3.6 standard deviations (0.8), and if the geometric distance for a test sample exceeds 4.0, then the sample may be flagged as containing rRBCs. Again, in this embodiment, a "score" may be provided that indicates the numerical distance between the value and the criterion if the value has met the criterion. In the embodiment shown in FIG. 5, if the value is meets the criterion (i.e., is at least 4.0), the sample can be flagged. The higher the difference between the value and the criterion, the higher the score.

Lymphocyte box count ratio

In a further embodiment, the data comprises the axial light loss (ALL) and intermediate angle scatter (IAS) values for cells of the test sample that are classified as lymphocytes. In this embodiment, the value is the inverse of the ratio comprised of: a) the number of cells classified as lymphocytes defined by pre-determined ALL and IAS limits, divided by b) the number of cells classified as lymphocytes defined by ALL and IAS limits that are adjacent to the pre-determined ALL and IAS limits for the test sample. In this embodiment, the criterion is based on the inverse of the ratio of the number of cells classified as lymphocytes defined by pre-determined ALL and IAS limits, divided by the number of cells classified as lymphocytes defined by ALL and IAS limits that are adjacent to the pre-determined ALL and IAS limits for the reference samples.

Figure 6:
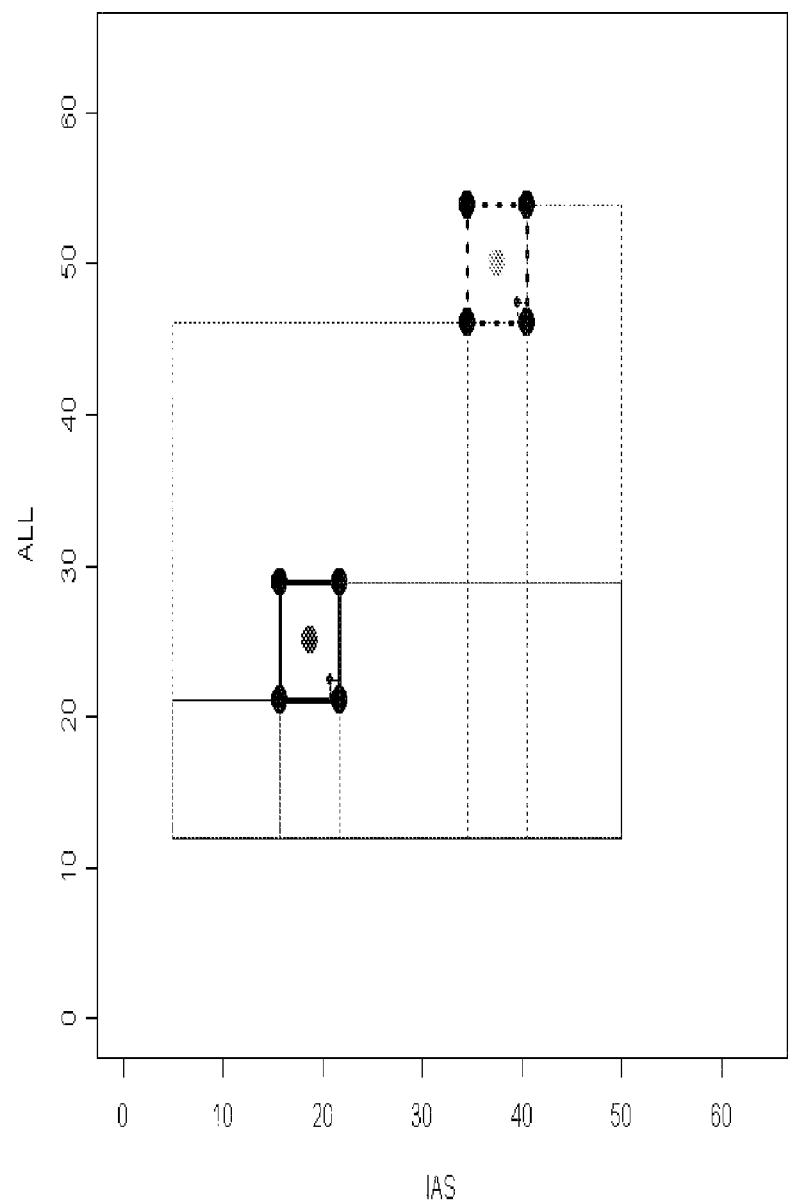
FIG. 6 is a graph showing exemplary positioning of boxes to determine a lymphocyte box count ratio.

As illustrated in the schematic scatter plot of FIG. 6, the cells classified as lymphocytes defined by pre-determined ALL and IAS limits are indicated in the lower left box that contains a spot. The number of cells classified as lymphocytes within the box (the "true" lymphocytes) are compared to the numbers of cells in one or more adjacent boxes, i.e., the "un-true" lymphocytes. As shown in FIG. 6, the un-true lymphocytes are defined by an adjacent box to the left of the true lymphocyte box, an adjacent box below the true lymphocyte box and/or an adjacent box that is to the right of the true lymphocyte box) to define one or more cell number ratios. As noted, all of the adjacent boxes have defined upper and lower IAS and ALL limits, which limits share either a side, part of a side, or a corner with the "true"-lymphocyte box.

The pre-determined ALL and IAS limits for the true lymphocyte box are defined by the median of the mean ALL and mean IAS values for cells classified as lymphocytes in a plurality of prior samples run on the analyzer (using e.g., data from at least the prior 5, 10, 50, 100, 200, 500, 1,000, or 10,000 normal samples analyzed by the hematology analyzer), plus and minus at least 1 standard deviation (e.g., at least 2, at least 2.5, at least 3 up to 4, 5 or 6 or more standard deviations) from the means. As shown in FIG. 6, the median of the mean IAS value for the cells classified as lymphocytes in the prior samples is approximately 19 and, since the standard deviation is approximately 3, the and lower and upper IAS limits for the cells classified as lymphocytes are approximately 16 and 22, respectively. Likewise, the median of the mean ALL value for the lymphocytes in the prior samples is approximately 25 and, since the standard deviation is approximately 4, the lower and upper IAS limits for the lymphocytes are approximately 21 and 29, respectively. Since the size of the true lymphocyte box can change and the position of the box can move depending on the prior samples, then the size and position of the adjacent boxes can, too, change to maintain a corner or edge in common with the lymphocyte box; this is schematically indicated by the second lymphocyte box with dashed edges in FIG. 6, and its corresponding adjacent boxes.

In a particular embodiment, the total number of lymphocytes defined by adjacent ALL and IAS limits (i.e., the total number of cells in the one or more adjacent non-true lymphocyte boxes) is divided by the number of lymphocytes in the pre-determined ALL and IAS limits (i.e., the number of cells in the true lymphocyte box) to define a single ratio that describes the lymphocyte box count ratio.

While this ratio can itself indicate that the sample may be an outlier if it is sufficiently large relative to other prior samples (thereby indicating that the test sample contains rRBCs), the ratio can be compared to a static criterion that is based on the mean lymphocyte box count ratio for cells that are classified as lymphocytes in each of the reference samples plus at least one standard deviation (e.g., at least 2, at least 2.5, at least 3 up to 4, 5 or 6 or more standard deviations) from the mean.

Again, in this embodiment, a score can be provided that indicates the numerical distance between the value (which is the ratio discussed above) and the criterion (which can be based on the mean and standard deviation of the ratio of a collection of reference samples). In the embodiment shown in FIG. 7, if the value meets the criterion (i.e., is at least 0.8), the sample can be flagged. The higher the value is relative to the criterion, the higher the score.

Lymphocyte DSS

Figure 8:
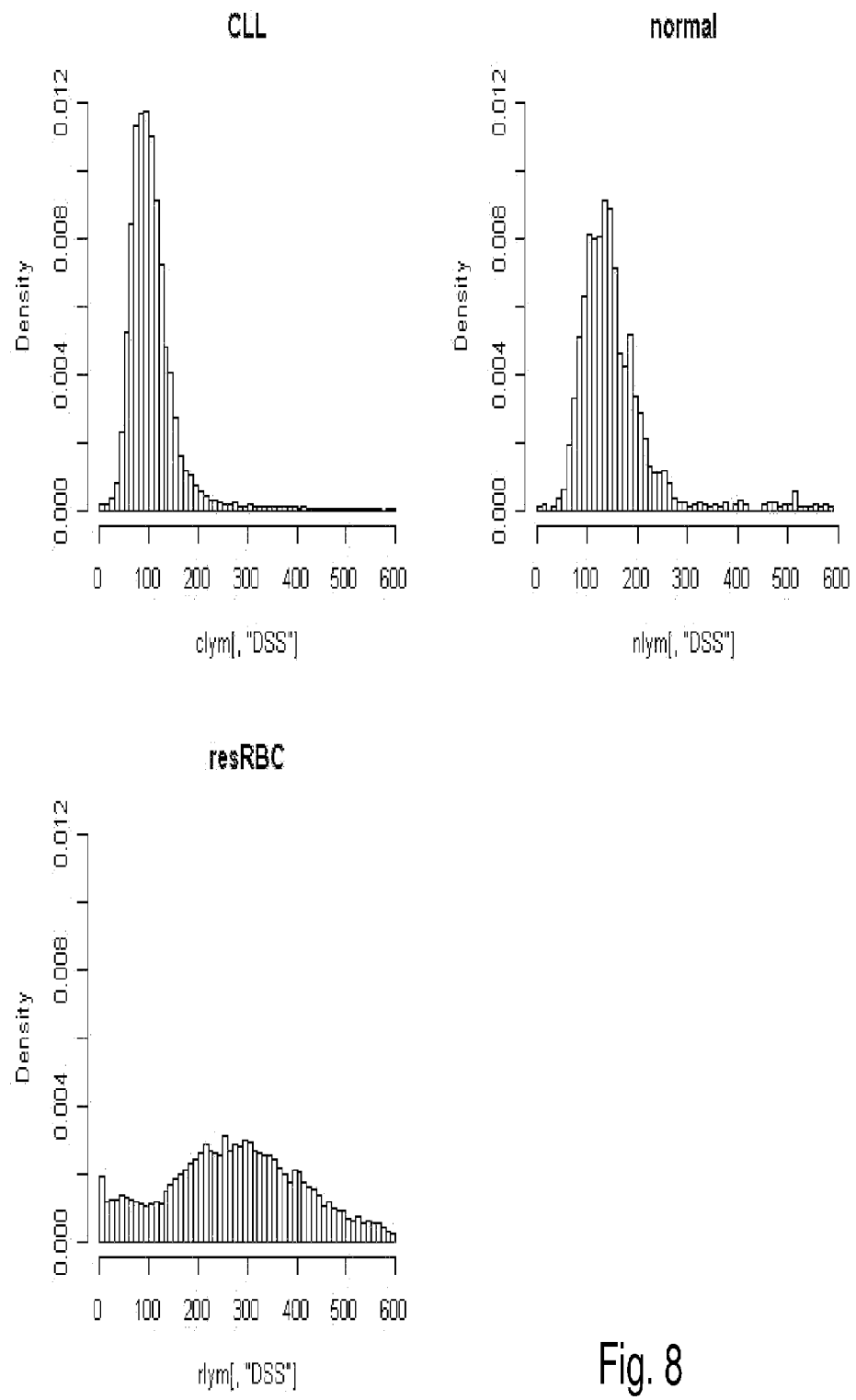
FIG. 8 is a set of three histograms showing the distribution of lymphocytes in the depolarized side-scattering detection channel for sets of chronic lymphocytic leukemia, normal and lysis-resistant erythrocyte samples.

In another embodiment, the data comprises depolarized side scatter (DSS) values for cells classified as lymphocytes, the value compared to the criterion indicates the degree of distribution and/or skew of the DSS values for the test sample, and the criterion is based on the degree of distribution and/or skew of DSS values for the reference samples. In this embodiment, the DSS values for cells classified as lymphocytes are binned, and the bins are analyzed to determine the distribution width of the DSS values. As shown in FIG. 8, rRBCs have a wider distribution than normal cells, whereas chronic lymphocytic leukemia (CLL) cells have a narrower distribution. In a similar way (using different statistical methods) the DSS bins can be analyzed to determine the skew of the DSS values, where, as shown in FIG. 8, lymphocytes from both normal and CLL samples have a relatively normal distribution relative to that of a sample containing rRBCs.

Figure 9:
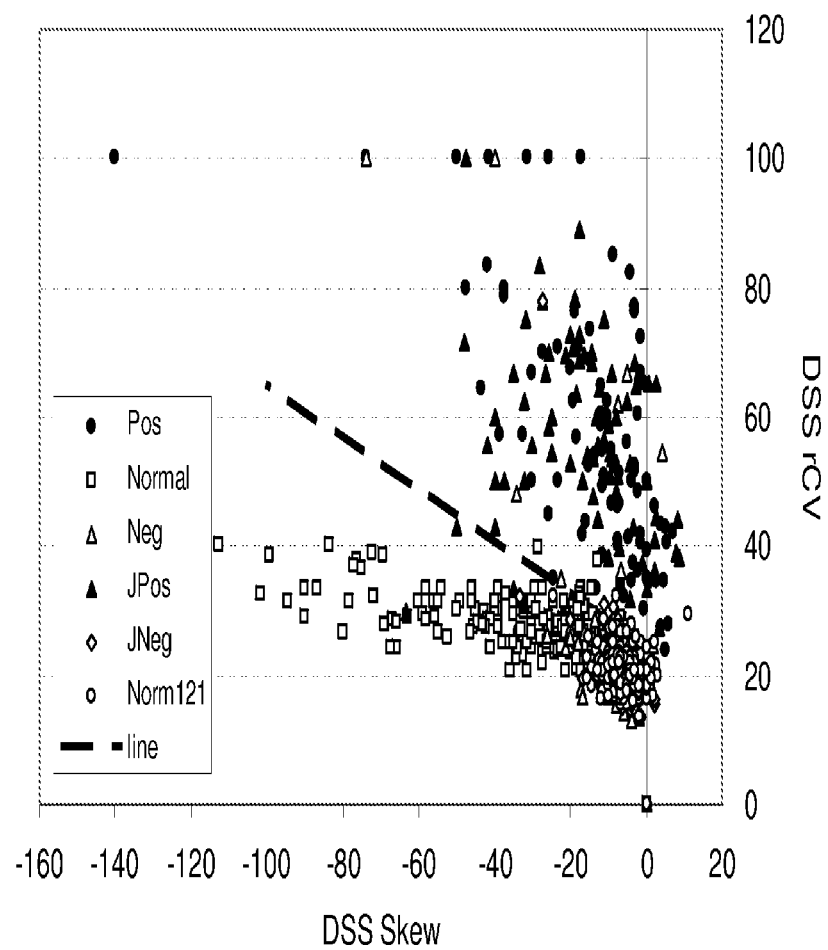
FIG. 9 a graph plotting the depolarized side-scattering coefficient of variation and skew for several samples.

In one embodiment, illustrated in FIG. 9, the value used for comparison to the criterion is based on the DSS distribution and DSS skew, where samples are plotted on a scattergram where DSS distribution and DSS skew form two axes, and the value is the signed geometric distance from a predetermined line ("line") on this scattergram (i.e., positive if the sample is above the line and negative if below it). Various types of samples are plotted in this graph, including sample sets that include predominantly normal samples ("Norm," "Norm121"), sets that include predominantly negative (i.e., non-rRBC-containing) samples ("Neg," "JNeg"), and other sets that include predominantly abnormal (i.e., rRBC-containing) samples ("Pos," "JPos"). In other embodiments, the DSS distribution and the DSS skew may be used independently to flag a sample.

While this value can itself indicate that the sample is an outlier if it is sufficiently large relative to other prior samples (thereby indicating that the test sample contains rRBCs), the value can be compared to a static criterion based on the mean DSS distribution and/or mean DSS skew for cells that are classified as lymphocytes in each of the reference samples plus at least one standard deviation (e.g., at least 2, at least 2.5, at least 3 up to 4, 5 or 6 or more standard deviations) from the mean. In the embodiment shown in FIG. 10, the mean and standard deviation of the DSS-derived values is −6.6 and 2.2, respectively, which provides a criterion of 0.

Again, in this embodiment, a "score" can be provided that indicates the numerical difference between the value and the criterion if the value meets the criterion. In the embodiment shown in FIG. 10, if the value meets the criterion (i.e., is at least 0), the sample can be flagged. The higher the value is relative to the criterion, the higher the score is awarded.

In another embodiment, the data comprises the depolarized side scatter (DSS) values for cells classified as lymphocytes, the value indicates the number of zero-bin events in the distribution of the DSS values (where a "zero-bin event" is an event classified in the first digitization bin, i.e., bin "zero," of the available range for digitization) and the criterion is based on the number of zero-bin events in the distribution of DSS values for the reference samples. Again, a score can be provided that indicates the numerical difference between the value and the criterion, if the value meets the criterion.

Combined Scores, Weighting and Cross-Checking

As noted above, each of the methods can generate a numerical score that describes the difference between the test sample and the reference sample. In certain embodiments, these scores can be summed, and the blood sample can be flagged if the summed score exceeds a threshold. The individual scores can be weighed prior to summing. In particular embodiments, if a value does not meet a criterion, then it may be scored as a "0", and, as such, will not contribute to the sum of the scores.

In certain embodiments, in addition to directly detecting rRBCs, the method may also estimate the accuracy of the WBC count using the impedance RBC assay (RBCi) and the reticulocyte (RETC) assay.

In one embodiment, the impedance RBC histogram contains mostly WBCs in the uppermost digitization bins (e.g., last bin, last 5 bins, etc.) of the digitization range, and this cross check makes sure that the WBC/RBC ratio, which can be obtained from the histogram, is not significantly lower than that obtained from the WBC concentration (from the WBC assay) and the RBC concentration (from the RBCi assay). If the WBC/RBC ratio from the RBCi histogram is significantly lower than the WBC/RBC ratio from the WBC and RBCi assays, the rRBC flag is raised.

In other embodiments, the cells in the sample are separated into WBCs, RBCs and PLTs in the RETC assay on the basis of scatter patterns in FL1 vs. IAS. The crosscheck uses the ratio of the WBCs to the RBCs in this assay, which is compared to the WBC/RBC ratio from the WBC and RBCi assays described above. If the ratio from the RETC assay is significantly lower than the ratio from the WBC and RBCi assays, the rRBC flag is raised.

Programming

In one embodiment, a physical memory containing instructions (i.e. "programming") for performing the method described above is provided. In some embodiments, the memory can comprise a physical computer-readable medium comprising programming to flag a blood sample as containing resistant red blood cells or fragile white blood cells by: analyzing data for test blood cells analyzed by said hematology analyzer to produce a value that describes a characteristic of said test blood cells; comparing the value to a criterion obtained from analysis of a plurality of reference samples comprising reference blood cells; and flagging the blood sample as containing resistant red blood cells or fragile white blood cells if the value meets the criterion, as described above.

The programming can be provided in a physical storage or transmission medium. A computer receiving the instructions can then execute the algorithm and/or process data obtained from the subject method. Examples of storage media that are computer-readable include floppy disks, magnetic tape, CD-ROM, a hard disk drive, a ROM or integrated circuit, a magneto-optical disk, or a computer readable card such as a PCMCIA card and the like, whether or not such devices are internal or external to the computer. A file containing information can be "stored" on computer readable medium, where "storing" means recording information such that it is accessible and retrievable at a later date by a computer on a local or remote network.

The method described above can be automatically executed each time a sample is run.

Utility

The hematology analyzer described above can be employed to identify and flag samples that contain fragile leukocytes (fWBC) or lysis-resistant red blood cells (rRBCs).

Fragile Leukocytes

In certain cases the leukocytes in a blood sample are particularly fragile to lysis, and can be lysed in whole or in part by the erythrolytic agent. As noted above, the method described above can be used to flag a blood sample as containing fragile white blood cells.

In a few rare but very important clinical disorders, certain circulating leukocyte sub-populations may contain extremely lyse-sensitive members. "Fragile lymphocytes", as in certain cases of chronic lymphocytic leukemia and as in infectious mononucleosis, are a paradigm for this situation. In such clinical conditions, the morphologists of the last century identified "Gumprecht shadows" in the microscopic analysis of the blood film. (See H. Begemann, J. Rastetter, *Atlas of Clinical Hematology*, 4th Edition 1989, p. 227, Springer-Verlag). Today's technologists recognize "smear cells" (J. Cross, C. A. Strange, "Erroneous Ortho ELT 800/WS WBC in chronic lymphatic leukaemia," *Clin. Lab. Hematol.* 1987, 9, 371-375) or "smudge cells" (National Committee for Clinical Laboratory Standards, *Reference Leukocyte Differential Count (Proportional) and Evaluation of Instrumental Method*, Approved Standard, NCCLS Document H20-A 1992, Villanova, Pa.). The affected leukocyte cell populations may contain cells so fragile that they cannot even be preserved in the blood film without the addition of a high concentration of a colloid (such as albumin) to the droplet of blood before the stress of the film-making process is imposed on the cells. (See, e.g., NCCLS Document H20-A; and Densmore, C. M., "Eliminating disintegrated cells on hematologic films," *Lab. Med.* 12:640-41, 1981.)

Such very fragile leukocytes are also difficult to preserve when blood is greatly diluted and vigorously processed in flow-cytometric automated blood cell counters. This is true even when the diluent is an apparently balanced, (protein-free) physiologic salt solution that is intended to preserve rather than lyse the numerous interfering erythrocytes. Hence, when these fragile leukocytes are present in a sample, it is sometimes virtually impossible to know the correct circulating leukocyte concentration (or the total white cell count) and the correct numerical count for the leukocyte subpopulations. (See, e.g., J. Cross, C. A. Strange, "Erroneous Ortho ELT 800/WS WBC in chronic lymphatic leukaemia," *Clin. Lab. Hematol.* 1987, 9, 371-76; J. B. Dixon et al., "Electronic Counting of Dog Leukocytes Discrepancies Arising From Calibration With Coulter Standard 4C and With the Hemocytometer," *Res. Vet. Sci.* 31 (2), 1981, 249-252; and J. M. England, et al., "An assessment of the Ortho ELT-8," *Clin. Lab. Hematol.* 1982, 4, 187-99.)

Resistant Erythrocytes

In certain cases the red blood cells in a blood sample are particularly resistant to lysis, and are not fully lysed by the erythrolytic agent. As noted above, the method described above can be used to flag a blood sample as containing lysis-resistant red blood cells.

In one group of well-known conditions that lead to lysis-surviving erythrocytes, the erythrocytes themselves appear difficult to lyse by the techniques applicable to typical human samples; examples of these conditions include sickle cell diseases, liver diseases, thalassemias, and other atypical, aberrant physiologic mammalian erythrocyte populations. Erythrocytes of normal and healthy neonates and infants also exhibit significant degrees of lysis resistance. In another group of conditions or disorders, the presence of lysis-opposing interfering substances makes erythrocytes difficult to lyse under erythrolytic conditions that are effective for typical human samples. For example, an abnormally high concentration of blood proteins tends to neutralize some of the erythrolytic agents and to oncotic ally counteract some of the erythrolytic physical approaches. (See, e.g., A. Bremmelgaard, J. Nygard, "Interference by Cryoglobulins with White Blood Cell Measurements on Coulter Counter," *Scand. J. Clin. Lab. Invest.* 51 (5) 1991, 489-492.) Parenteral feeding solutions, certain blood lipid disorders and therapeutic drugs can also act to create erythroprotective conditions, either alone or in combination with other agents or with anomalous erythrocytes.

In the presence of failed or partial erythrolysis resulting from the problem of lyse-resistant erythrocytes, the entire leukocyte counting procedure may become invalid for affected samples. Lyse-surviving erythrocytes interfere with leukocyte visualization. If one percent of five million erythrocytes fails to lyse for every microliter of human blood, fifty thousand unlysed erythrocytes remain to obscure the five thousand nucleated leukocytes present in that representative microliter of human blood.

EXAMPLES

The current method for determining the White Blood Cell (WBC) concentration and differential on the CELL-DYN Sapphire® hematology analyzer requires the lysis of Red Blood Cells (RBCs). A lysing agent, saponin, is a component of the WBC part A reagent. On normal specimens, this agent is effective in lysing the RBCs, and so the WBC concentration and differential are accurate. However, some demographics (neonatal/pediatric) and pathologies (sickle cell anemia, liver disease) can cause changes to the RBCs that make them resistant to the lysing agent. When this occurs, the apparent WBC concentration, lymphocyte concentration, and lymphocyte percentage can be falsely elevated. If this condition is detected, the WBC and differential results on the patient report are invalidated, and the "resistant RBC" (rRBC) flag is set. An algorithm for detecting rRBC is described below.

1. rRBC Flagging Algorithm

The rRBC flagging algorithm uses one or more criteria to determine if the flag should be set. The criteria are:
1) Declining total cell count rate over a fixed first period of the WBC assay, e.g, the first 9 seconds.
2) Declining lymphocyte ("lymph") count rate over the WBC assay. The lymph events from the FCS file, up to time mark 1126 after the start time, are used. (In this embodiment, FCS file list mode time marks are 8 millisec (ms) apart; 8 ms*1126 intervals~9 seconds.) For all of the following criteria the entire set of list mode data is used.
3) Instrument lymphocyte population position in (IAS, ALL) space compared with a running median of the last 51 normal patient runs in CBC or CBC+RETC test selection (a test selection configures the analyzer to execute a certain combination of assays; the CBC test selection, for example, includes, among others, the RBCi assay and the WBC assay run with standard lysis strength; the CBC+RETC test selection additionally includes the RETC assay).
4) Ratio of lymphocytes within the expected area of the scattergram to lymphocytes in neighboring areas.
5) Distribution of lymphocytes in DSS. Normal and chronic lymphocytic leukemia (CLLs) samples have a narrower distribution with lower skew.
6) Number of counts in the zero bin in DSS. A rRBC sample has more counts in this bin than a normal sample.

The rRBC flagging algorithm is executed before the nucleated RBC (NRBC) algorithm is run. The NRBC algorithm sometimes can change the classification of events from lymph to NRBC and vice versa. All of the events that are affected by the NRBC algorithm are positive in FL3. The rRBC algorithm is mostly concerned with rRBC particles that are dim in FL3 and therefore may not be considered by the NRBC algorithm. The goal of the rRBC algorithm is to issue an invalidating flag if there is strong evidence that rRBC particles are present.

In addition to the direct measures for the presence of rRBCs, the algorithm checks the final WBC count by looking at an estimated WBC count from the RBCi assay and the RETC assay, if part of the test selection for the sample at hand.

2. Data for Calibration

All data used to develop and test the algorithm was collected on 14 analyzers located in Japan and 3 analyzers located in the Netherlands.

The data from two analyzers were used to determine the normal values for all rRBC flagging criteria. Data for 1031 normal samples were collected using one analyzer in the Netherlands, and data for 2063 samples were collected using another analyzer in Japan. Criteria for normal samples were:
Specimen Type=Patient
No invalidated data
Numerical results within the following ranges:
3.9<WBC<10.0 k/μL
38.0<% NEU<80.0
15.0<% LYM<40.0
0.0<% MON<13.0
4.2<RBC<5.7 M/μL
80.0<MCV<97.0 fL
11.0<RDW<15.0% CV
140.0<PLT<390.0 k/μL
13.2<HGB<16.9 g/dL 3. Algorithm criteria 3.1 Total Count Rate Slope During the WBC portion of a test cycle, the CELL-DYN Sapphire® system logs the number of total events (signals that qualify based on the triple trigger settings) in the hardware counter. At 100 millisecond (ms) intervals, the accumulated total event count is captured to form a data series known as the WBC hardware event count data, which will be referred to here as the "total count data" (where total refers to the totality of WBCs, as opposed to subpopulations thereof, such as, e.g., lymphocytes). The WBC portion of a test cycle varies in length according to the test selection, but it is at least 9 seconds long in all cases.

The total count rate slope criterion is based on first 9 seconds of the total count data. In these data a declining rate is sought: a significantly negative slope when the instantaneous total count (delta between successive total count data values) is plotted against the incremental 100 msec intervals. The slope of a straight-line fit through the 9 seconds' worth of instantaneous total count data should be significantly lower than zero. The actual threshold (which is interpreted as 'significant') before a score is generated comes from the distribution of normal samples in the algorithm development data set. The normal samples have a WBC total count data slope of 0.02±0.03 (mean±standard deviation). The algorithm uses the 3-sigma level below the normal mean of the reference cells, −0.07, as the threshold below which the total count rate slope criterion contribution score is accumulated. This is illustrated in FIG. 2.

For each sample measured, the algorithm uses a straight-line fit to obtain the slope and its standard deviation, or sigma, a measure of the uncertainty of the slope value. The algorithm uses the slope plus 3 times its sigma as the value used for the slope of the total count rate to compare to the threshold. The algorithm normalizes the slope by the total number of hardware counts. The score for this criterion is proportional to the difference between the final slope and the threshold value, if the final slope is more negative than the threshold, and zero if the final slope isn't more negative than the threshold.

Figure 3:
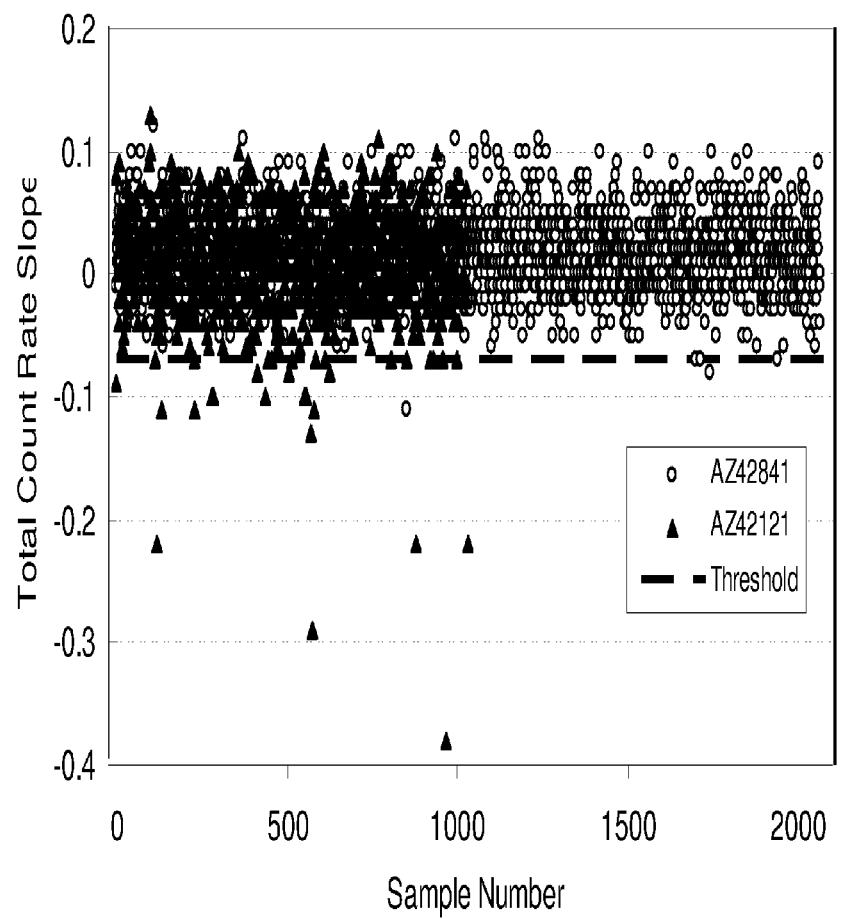
FIG. 3 is a plot showing total-count slopes for a set of normal reference samples and the threshold below which a flagging score is accumulated.

The plot of FIG. 3 shows all total count slopes for normal samples in a training set and the threshold below which a rRBC score is accumulated. There are a few samples below the threshold, which will be accumulating a rRBC score.

3.2 Lymphocyte Count Rate Slope

The total slope includes all events counted, including neutrophils and any surviving red blood cells (RBCs), both of which make the slope not as sensitive to detecting RBC interference in the lymphocytes. The total slope can be negative due to rRBC events that have already been classified as RBCs (and therefore do not interfere with either the lymphocyte count or the WBC count). On the other hand, the total slope can be close to zero due to, e.g., high percentages of neutrophils or another cell population, even while rRBCs alter the lymphocyte count. Therefore the algorithm is interested in what the count rate slope is for events classified as lymphocytes. The algorithm takes those events, and uses the time variable in the FCS data to create a count rate histogram for the lymphocytes only. In this embodiment, each time stamp in the FCS file is 8 ms. A range of 0-1125 time stamps is used, corresponding to a total of 9 seconds. Those 9 seconds of list mode lymph data are binned into 30 bins and a lymph count rate for each bin is determined. Then a line is fitted to all bins (excluding those containing zero counts in order to avoid spurious skewing of the fit).

Figure 4:
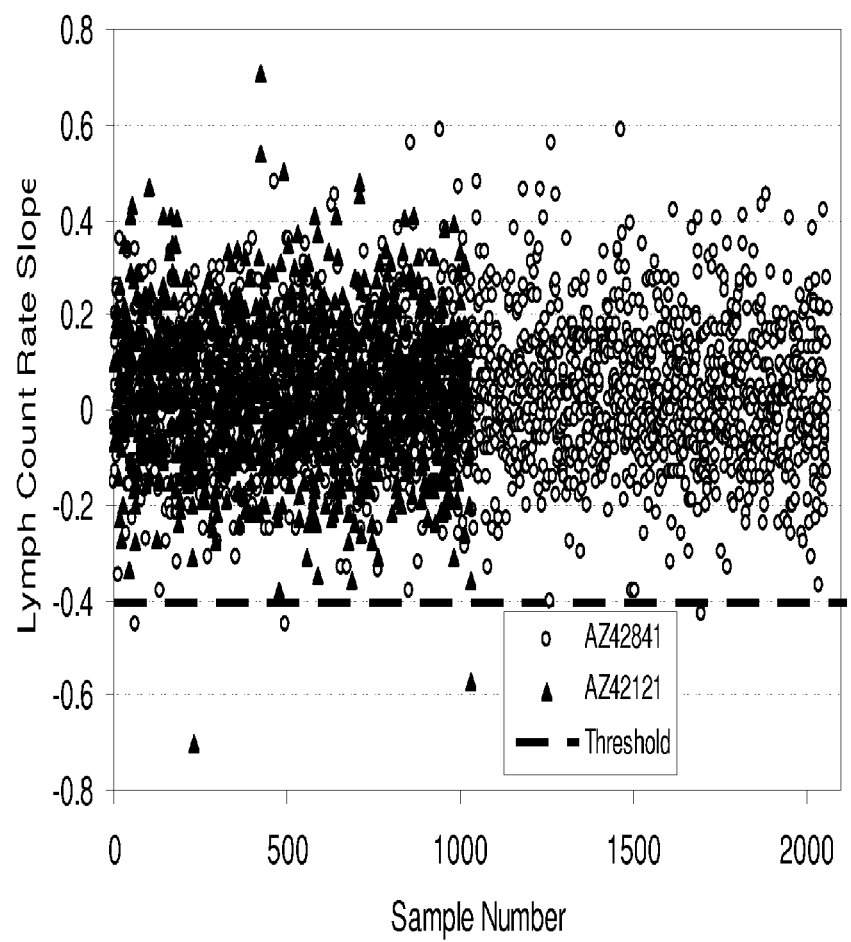
FIG. 4 is a plot showing lymphocyte slopes for a set of normal reference samples and the threshold below which a flagging score is accumulated.

The normal samples have a lymph slope of 0.04±0.15; the algorithm uses the 3-sigma level below the normal mean, i.e. −0.41, as the threshold. The slope for each sample is estimated, and three standard deviations from the sample line fit are added to the estimated sample slope. Finally the sample lymph slope is normalized by the total number of lymphocytes. This is shown in FIG. 4.

3.3 Lymphocyte Positions

The two lymphocyte positional checks aim to detect a population of rRBCs that is merged with and counted together with the lymphocytes. Often contamination by rRBCs shifts the location of the lymph population. The first positional check analyzes the mean position in ALL and IAS of the entire lymphocyte population.

3.3.1 Lymphocyte Mean Values History

The lymph positions (i.e., the ALL and IAS bin numbers of the mean of all lymphocyte events for each sample) are tracked over the most recent 51 normal samples. All samples that go into the set of 51 must satisfy all of the following criteria:

Specimen Type=Patient
Test selection=CBC or CBC+RETC
No lymph flags
Numerical results within the following ranges:
  3.9<WBC<10.0 k/µL
  38.0<% NEU<80.0
  15.0<% LYM<40.0
  0.0<% MON<13.0

Note that the rest of the hemogram results are not used here because only the WBC results are available to the algorithm at the time when the lymph position history is used and updated.

For a sample run in CBC and CBC+RETC test selections, the median of each history (ALL and IAS) is calculated and used for comparison with the current sample. For a sample run in CBC+RETC+R and CBC+R test selections (the CBC+RETC+R test selection is analogous to the CBC+RETC test selection, except that the WBC assay is run with a higher lytic strength; the CBC+R test selection is analogous to the CBC test selection, except that the WBC assay is run with a yet higher lytic strength than in the CBC+RETC+R test selection), the algorithm subtracts 9 bins (on a 256-bin scale) from the stored ALL median and 14 bins (also on a 256-bin scale) from the stored IAS median. The difference is due to the differences in mean lymph ALL and IAS positions between the normal-lysis-level test selections (CBC, CBC+RETC) and the higher-lysis-level test selection (CBC+RETC+R, CBC+R). The algorithm is only tracking the positions in the CBC and CBC+RETC test selections because the other test selections are not used as often.

The lymphocyte mean location history file consists of 51 pairs of ALL and IAS mean values. The median values of both the IAS mean history and the ALL mean history are also stored in the history file. The medians are calculated independently in IAS and ALL. Thus the median value in IAS can be affected differently from the median value in ALL as the history file is progressively updated.

When the lymphocyte mean history configuration file does not exist at software installation or startup (or after certain service events), the lymphocyte location history configuration file is created using existing configuration file support from the data station software. Defaults for ALL and IAS mean values are set to the current default positional values of ALL and IAS respectively. The default bin values are lymph ALL=100 and lymph IAS=75 (both on a 256-bin scale).

Pairs of ALL or IAS mean values are reset to the current default positional values (values for ALL and IAS) if either of the following is performed:
 a) a sample is run after the ALL or IAS Pre-Amp Gain or Amplifier Gain setpoints for Optical WBC are changed and activated;
 b) a sample is run after the default positional values for IAS or ALL are changed.

The lymphocyte mean location values are calculated for each WBC test run. If the specimen type is Patient (i.e., background and other special test runs are excluded) and test selection is CBC or CBC+RETC with no fault for the lymphocyte reportable data, the current lymphocyte mean values are stored in the lymphocyte mean history configuration file. Once the 51 pairs are filled, the oldest pair is removed, following the format first in, first out.

The medians of lymphocyte mean values from the history file are stored in the header of the FCS file.

3.3.2 Lymphocyte Geometric Distance

The algorithm compares the lymph positions, in (IAS, ALL) space, of any given sample to the median of the last 51 normal samples. The first test is the value of the Euclidean distance between the median location in (IAS, ALL) space from the history file and the location of the current sample's lymph position (i.e., the mean position, in IAS and ALL, of all lymph events in the current sample). FIG. 5 is the distribution of this distance for the normal samples from the training set. The threshold is 4.0, which is an approximation to the ensemble mean (1.1) plus 3-sigma level (0.8). All distance calculations are done on a 64-bin scale to limit memory usage. This leads to a fairly low resolution, which is visible in the distribution of the data.

Other options for implementation include employing additional detection channels beside ALL and IAS (e.g., PSS, DSS, or fluorescence channels) in describing lymphocyte positions in multidimensional space; in this case, the geometric distance between the median reference lymphocyte position and the test sample lymphocyte position is again calculated as a Euclidean distance, but over as many dimensions as the number of detection channels employed in describing such positions.

3.4 Lymphocyte Box Count Ratio

The second test based on lymph position information compares the counts in a box where the lymphocytes are normally expected to be with the counts in a series of boxes around the expected lymph position. In FIG. 5 the relevant boxes and positions are illustrated. All box corners that are adjustable are marked with a solid dot. The other box boundaries adjust only to follow the adjustable corners. Marked in red is the median location of the lymph means history, as tracked by the last 51 normals. To show how all the other boxes move when the lymph median location moves, we show a second lymph median location marked with a green dot. The 4 corners of the "true" (expected) lymphocyte box are calculated from the median location, converted to a value on a 64-bin scale to limit memory usage, by adding or subtracting 3.0 (also on a 64-bin scale) in IAS and 4.2 (again on a 64-bin scale) in ALL. Those numbers are the 3-sigma values of the distribution of normals in IAS and ALL from the algorithm development sample set. This determines the location of the expected lymphocyte box, which is shown in black.

The box score ratio is the count of lymphocytes in the blue boxes ("non-true" lymphocyte) divided by the count in the black box ("true" lymphocyte). This is illustrated in FIG. 6.

Figure 7:
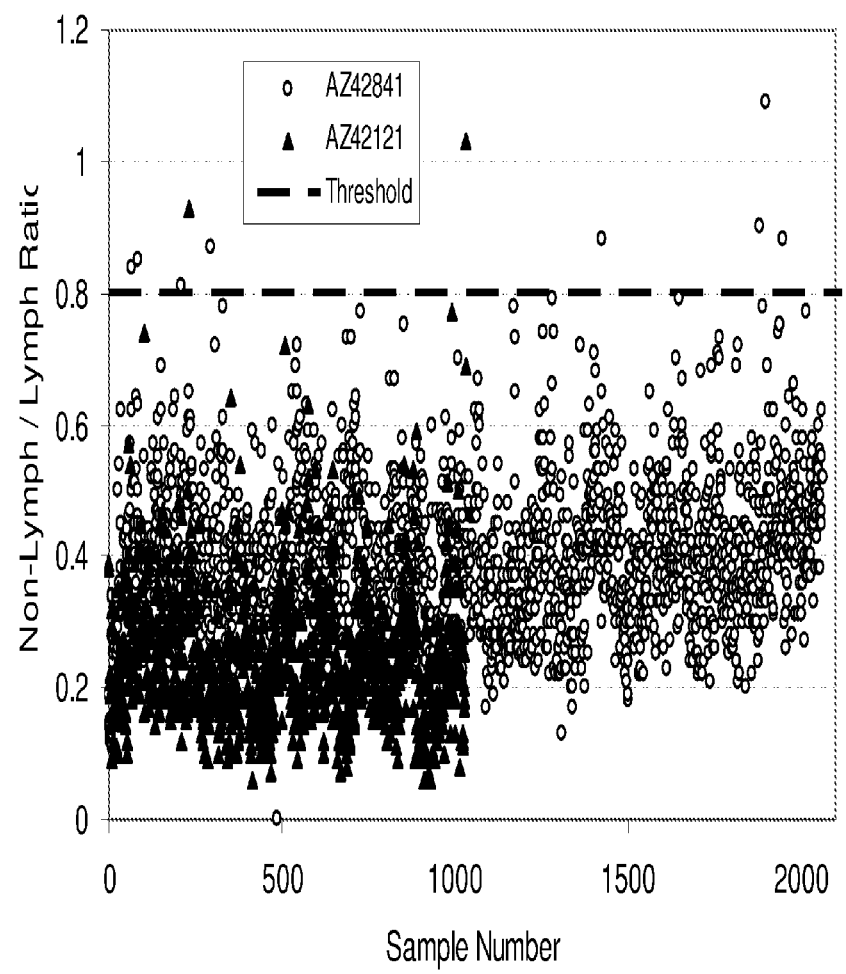
FIG. 7 is a graph showing the distribution of box count ratios for a set of normal reference samples and the threshold above which a flagging score is accumulated.

The two analyzers used to establish the criterion threshold show a noticeably different distribution of box count ratios. The 42841AZ analyzer has consistently higher non-lymphocyte to lymphocyte ratios than the 42121AZ analyzer. This is most likely due to a difference in optical alignment between the two analyzers in the training set. The 42841AZ analyzer has more spread-out populations, resulting in more counts in the non-lymphocyte boxes. Other analyzers were checked and it was found that 42841AZ analyzer has a higher average box count ratio than most. Therefore the threshold value was based on its performance, in order to avoid excessive flagging in analyzers with similar performance. The mean and SD of the distribution of box count ratios for the 42841AZ analyzer are 0.39 and 0.11, respectively. The algorithm threshold value was set at 0.8, which is an approximation of the mean plus 3-sigma value. This is illustrated in FIG. 7.

3.5 DSS

A linear DSS histogram of the lymphocyte events was employed. This histogram is analyzed for its median, robust SD (rSD)=median (|x−median (x)|), and $10^{th}$ and $90^{th}$ percentile. The normalized counts in the zero bin (i.e., the number of events classified in the first digitization bin of the available range, scaled by the total number of events in the distribution) are also used. In FIG. 8 the DSS histogram for known CLL, normal and rRBC samples are shown.

The histograms show that:
the rRBC sample has a much broader distribution;
the rRBC sample has greater skew; and
the rRBC sample has a higher normalized number of counts in the zero bin.

3.5.1 DSS Distribution Width and Skew

The distribution width is parametrized by the robust CV measure (rCV), defined as rCV=(100*rSD/median). The skewness measure is skew=(2*median−$10^{th}$ percentile−$90^{th}$ percentile). Using those two numbers the algorithm calculates the first score for the DSS section: It is the geometric distance from a line in the (skew, rCV) space. The numerical value for this distance is d=(0.4*skew+rCV−25). In the graph of FIG. 9 the line is shown together with normal, positive, and negative sample sets.

Figure 10:
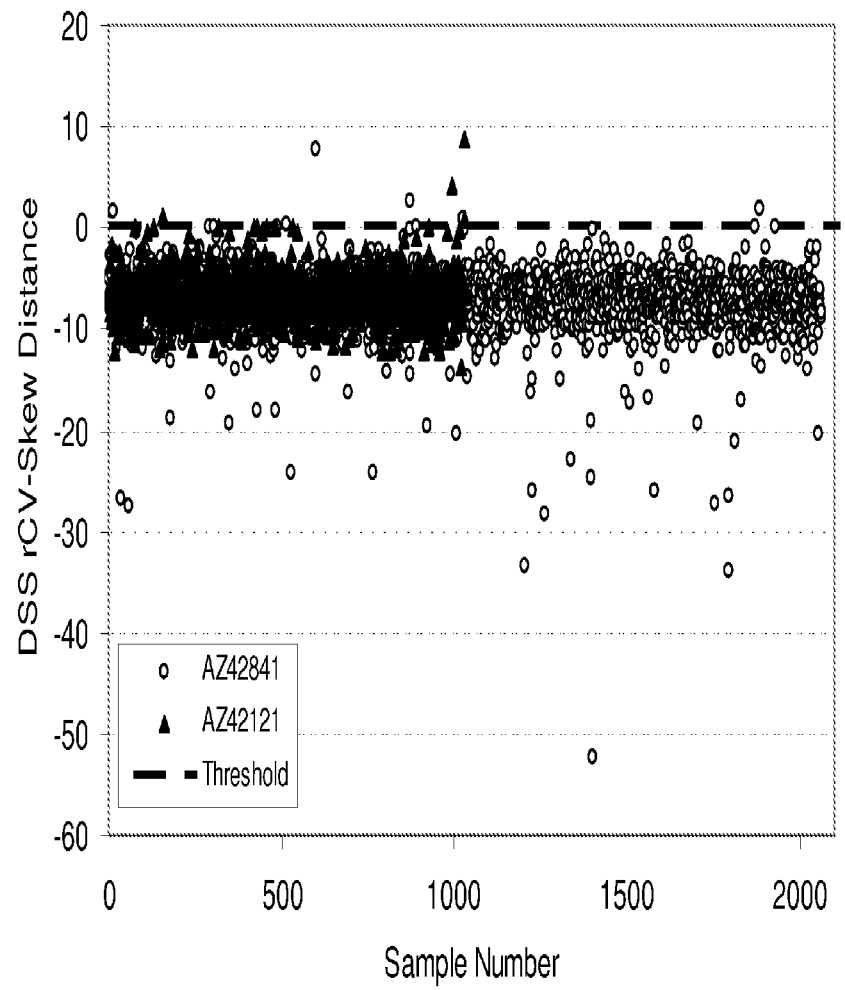
FIG. 10 a graph showing the values of a metric based on depolarized side scattering for a set of normal reference samples and the threshold above which a flagging score is accumulated.

In FIG. 10 the values for d for the set of normal samples are shown. The mean and SD for this normal sample set are −6.6 and 2.2, respectively, which leads to a threshold of zero.

3.5.2 DSS zero-bin measure

The second DSS measure is a measure based on the event counts in the DSS zero bin. The zero-bin measure is "scaled zero-bin"=[zero-bin counts*median*median/(total lymphocyte counts)]. The scaling by the median is an attempt to correct for the changes in the zero bin simply attributable to gain changes, or mean drifts, in DSS. Other scaling options are possible, and include additionally accounting for the standard deviation of the DSS distribution in order to model more accurately the predicted change in zero-bin value due to gain changes alone.

The median and SD for the zero-bin measure on the 42121AZ analyzer are 0 and 3.3, respectively, resulting in a threshold of about 10. Because with this threshold the zero-bin measure was observed to be more likely to cause false positive results than the other five measures, a second threshold of 20 was set. For any sample that results in a Scaled Zero-bin value below 10, the criterion does not contribute to the overall score for the rRBC flag. Between 10 and 20, the criterion contributes to the overall score, but not to the overall count of criteria met. Above 20, the criterion contributes to the score and to the overall met criteria count.

Figure 11:
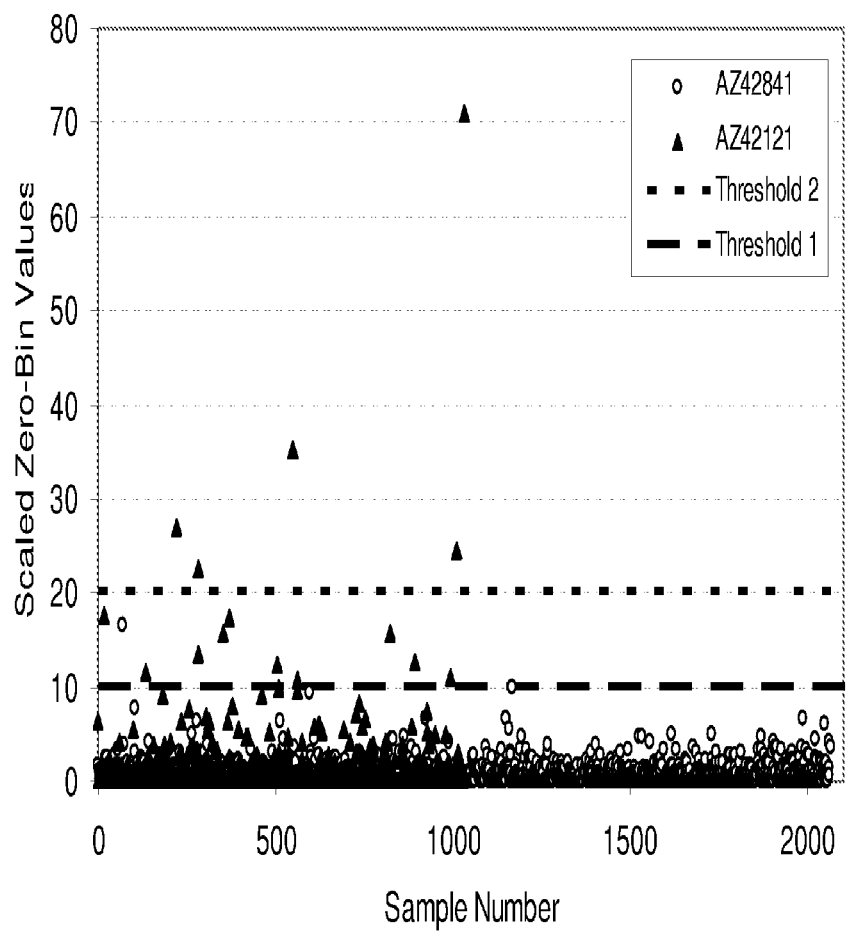
FIG. 11 is a graph showing the scaled depolarized side-scattering zero-bin values for a set of normal reference samples and two thresholds used in computing the flagging score and setting the flag.

In FIG. 11 the Scaled Zero-bin values for the normal sample sets are shown. The 42121AZ analyzer has many fewer normals than the 42841 analyzer, and even those samples called normals might include some rRBCs. The sample that has a score of 70 in the zero bin measure happens to accumulate more score from another criterion and actually trigger the rRBC flag to be set.

4. Combined Score

The scores from all six of the criteria detailed above are multiplied by their respective weights and then are added up for the final score. The weights have been determined by identifying 100 positive and 100 negative samples and then optimizing the weights to maximize the number of correct classifications.

| Feature | Weight |
| --- | --- |
| HW Slope | 122.5 |
| Lymph Slope | 404.8 |
| Lymph Peak Position | 16.0 |
| Lymph Box Count | 36.6 |
| DSS CV and Skew | #lymphocytes/200 |
| DSS Zero Bin | 1.0 |

The final test of the weights is performed by running the algorithm on large data sets and comparing the results to another rRBC flagging algorithm. This has been done extensively and the results show compellingly that the new algorithm performs better than the other algorithm.

5. Trigger Mechanisms

This algorithm requires that at least two criteria are above their respective thresholds. Then the algorithm computes the combined score as above, and the flag will be set if a weighted score of greater than 85 is reached. The flag will also be set, irrespective of the overall score, if 3 or more criteria are above their respective thresholds.

6. Scores for all Normal Samples

Figure 12:
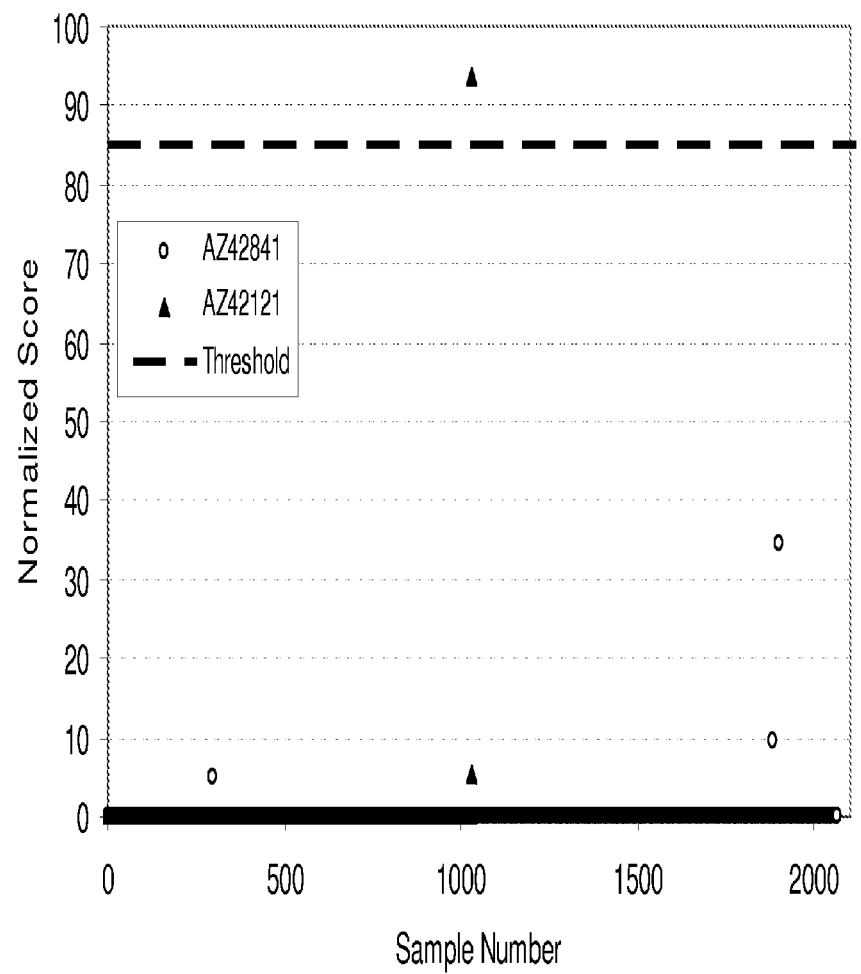
FIG. 12 is a graph showing flagging scores for a set of normal reference samples and the threshold used in setting the flag.

The graph of FIG. 12 shows the rRBC scores for all the normal samples. The scores are all zero except for five samples. One of the five samples did accumulate enough scores to trigger the rRBC flag.

7. RBCi Crosscheck

The impedance RBC (list mode) histogram contains mostly WBCs in its last bin. The cross check makes sure that the WBC/RBC ratio, which can be obtained from the impedance histogram, is not much lower than that obtained using the WBC concentration from the WBC assay and the RBC concentration from the impedance counts. The number of RBCs in the last bin increases as the MCV of the RBCs increases. Therefore the algorithm only uses the RBC histogram as a crosscheck if the MCV is less than 100 fL. For the samples with a lower MCV the RBC contribution to the last bin is estimated as (MCV−83)*0.7 normalized counts. There is no contribution if MCV is less than 83. The algorithm makes an estimate for the number of WBCs in the RBC histogram and compares that number to the reported WBC number. If the number from the RBC histogram is considerably lower than the WBC assay number, the rRBC flag is raised. As the MCV increases, the bar for the flag to be raised increases. The RBCi crosscheck never erases the rRBC flag.

Other options for implementation include using the measured red blood cell (size) distribution width, RDW, as a parameter in the cross check in addition to MCV; since a large RDW could cause the last bin to be populated with RBC events, the cross check would include an RDW threshold, to be used in conjunction with the measured MCV value, to determine the likelihood of RBCs being present in the last bin and only triggering the cross check if the likelihood is sufficiently low. Another option is to use a plurality of uppermost bins from the RBCi histogram to estimate the number of WBCs.

8. RETC Crosscheck

The RETC algorithm separates WBCs, RBCs and PLTs on the basis of scatter patterns in FL1 vs. IAS. The crosscheck uses the ratio of the WBC events to the RBC events in the RETC assay, which is compared to the ratio of WBC concentration to RBC concentration from the CBC assay. If the ratio from the RETC assay is significantly lower than the number from the CBC assay, the rRBC flag is raised in the CBC assay.

The RETC algorithm uses the RBC list mode count (from the RBCi assay) and the WBC list mode count (from the WBC assay). The rRBC crosscheck in the RETC algorithm calculates the upper limit to the WBC list mode count by taking the number n of WBC list mode events, calculating its sigma as sqrt(n), and then adding 3 sigma to the number of WBC list mode events. This increased WBC list mode event number is used to calculate the WBC/RBC ratio. It is intended as an upper limit to the true WBC/RBC ratio. This ratio is called WR_RETC. The CBC WBC/RBC ratio (which would be susceptible to overcounting of WBCs if undetected rRBCs are present) is called WR_CBC.

The algorithm calculates the difference ratio D=100* (WR_CBC−WR_RETC)/(WR_CBC+WR_RETC). If D is larger than 50, the rRBC flag is set. This choice of the limit on D means that the CBC WBC/RBC ratio needs to be at least 3 times as high as the upper limit of the RETC WBC/RBC ratio before the rRBC flag is set.

9. Second-Order Coefficients

Figure 13A:
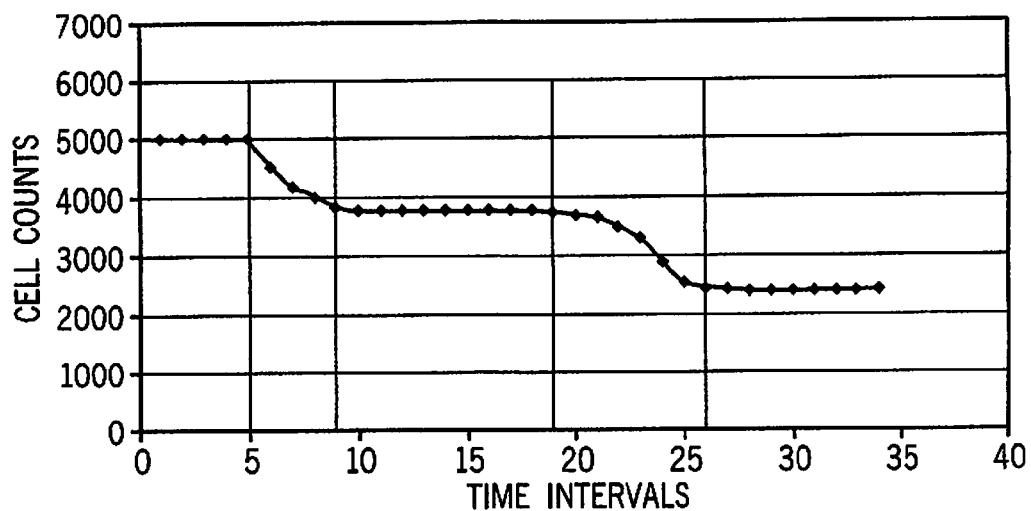
FIG. 13A-13C are graphs showing how the sign of the second-order coefficient of a line of best fit can be used to determine whether a sample contains rRBCs or fWBCs.
Figure 13B:
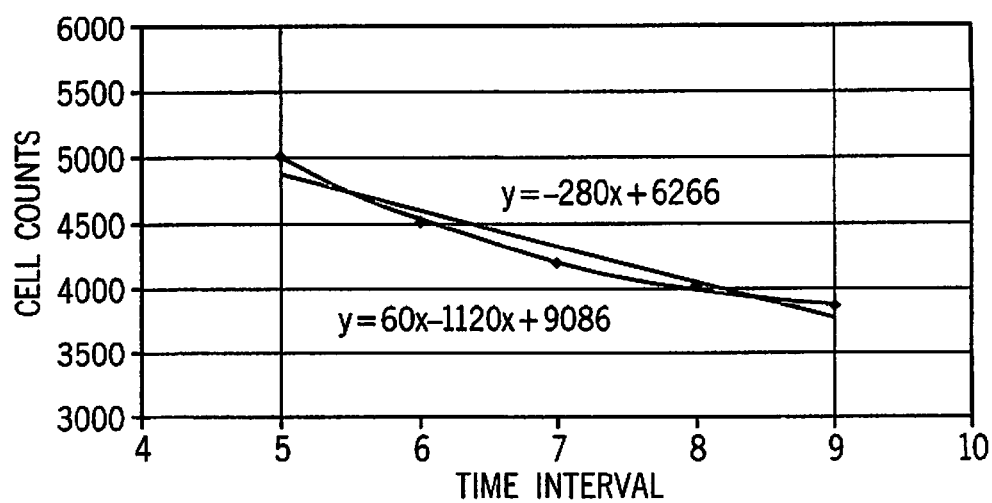
Figure 13C:
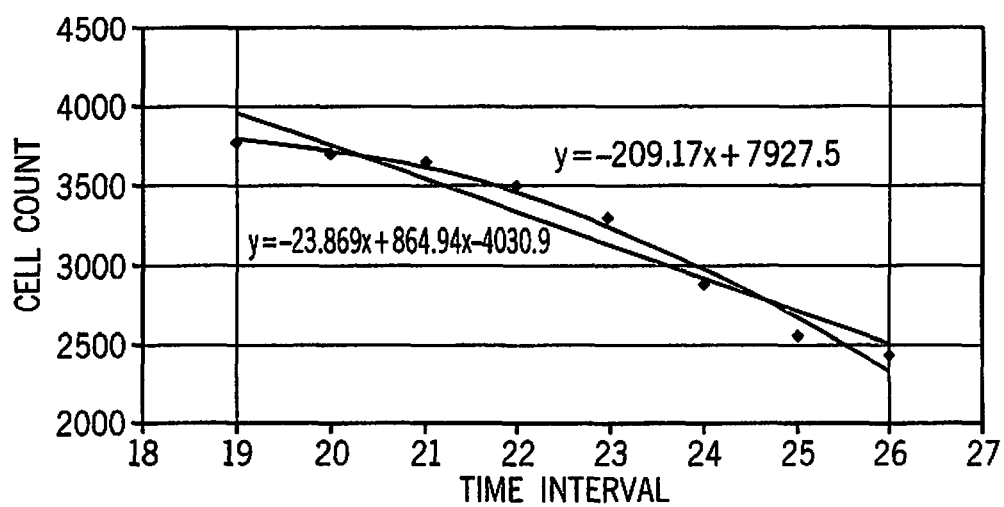

FIGS. 13A-13C illustrate how the sign of the second-order coefficient of the line of best fit can be used to determine whether a sample contains rRBCs or fWBCs. FIG. 13A shows a graph that illustrates the decrease in the total number of cells before, during and after the period in which the RBCs are lysed, and additionally before, during and after the period in which the WBCs are lysed. After addition of the erythrolytic agent, the RBCs lyse in the time period indicated by the vertical red lines. After a period in which the WBCs do not lyse (in the time period between the right hand vertical red line and the left hand vertical blue line), the WBCs start to lyse (in the time period between the vertical blue lines). FIG. 13B illustrates the decrease in the total number of cells in the time period in which the RBCs are lysing. In this period the line of best fit has a positive second-order coefficient (i.e., the rate of decrease in cell number is decreasing). FIG. 13C illustrates the decrease in the total number of cells in the time period in which the WBCs are lysing. In this period the line of best fit has a negative second-order coefficient (i.e., the rate of decrease in cell number is increasing).

All publications and patents cited in this specification are herein incorporated by reference as if each individual publication or patent were specifically and individually indicated to be incorporated by reference. The citation of any publication is for its disclosure prior to the filing date and should not be construed as an admission that the present invention is not entitled to antedate such publication by virtue of prior invention.

While the present invention has been described with reference to the specific embodiments thereof, it should be understood by those skilled in the art that various changes can be made and equivalents can be substituted without departing from the true spirit and scope of the invention. In addition, many modifications can be made to adapt a particular situation, material, composition of matter, process, process step or steps, to the objective, spirit and scope of the present invention. All such modifications are intended to be within the scope of the claims appended hereto.

What is claimed is:

1. A method for flagging a blood sample as containing lysis-resistant red blood cells or fragile white blood cells, the method comprising:
   (i) passing a blood sample through a flow cell of a hematology analyzer to generate a plurality of optical data using a plurality of detectors for detecting a plurality of optical characteristics of the blood sample, wherein the hematology analyzer comprises a light source for directing light to the flow cell;
   (ii) analyzing the optical data to determine one or more values for the blood sample, wherein the value is selected from the group comprising: a rate of decrease in the total number of cells in the blood sample over a period of time, a rate of decrease in the number of cells in the blood sample classified as lymphocytes over a period of time, a lymphocyte geometric distance, a lymphocyte box count ratio, or a lymphocyte depolarized side scatter (DSS) value; and
   (iii) calculating the difference between each value and a reference criterion that is based on data obtained from a plurality of reference samples, wherein if the value differs from the reference criterion by a predetermined amount, then the blood sample is flagged as containing lysis-resistant red blood cells or fragile white blood cells.

2. The method according to claim 1, wherein the plurality of detectors comprises one or more of: an axial light loss (ALL) detector, an intermediate angle scatter (IAS) detector, and a depolarized side scatter (DSS) detector.

3. The method according to claim 1, wherein the reference criterion is a static criterion.

4. The method according to claim 3, wherein the static criterion is based on data obtained from a number of reference samples ranging from 5 to 100,000.

5. The method according to claim 4, wherein the plurality reference samples were previously run on a different hematology analyzer.

6. The method according to claim 1, wherein the reference criterion is a continuously updated criterion that is updated each time a normal sample is analyzed by the hematology analyzer.

7. The method according to claim 6, wherein the continuously updated criterion is based on data obtained from a number of normal samples ranging from 5 to 10,000.

8. The method according to claim 7, wherein the plurality of normal samples comprises at least 50 normal samples.

9. The method according to claim 1, wherein the value is a lymphocyte geometric distance that is based on a mean axial light loss (ALL) measurement and a mean intermediate angle scatter (IAS) measurement of a cell in the blood sample that is classified as a lymphocyte, and wherein the reference criterion is a median of the mean ALL and mean IAS measurements in a plurality of reference samples.

10. The method according to claim 1, wherein the value is a lymphocyte box count ratio that is the inverse of the ratio of:
   a) the number of cells classified as lymphocytes in the blood sample as defined by a predetermined axial light loss (ALL) limit and a predetermined intermediate angle scatter (IAS) limit; divided by
   b) the number of cells classified as lymphocytes in the blood sample as defined by a predetermined axial light loss (ALL) limit that is adjacent to the ALL limit in a) and a predetermined intermediate angle scatter (IAS) limit that is adjacent to the IAS limit in a); and wherein the reference criterion is based on the inverse of the ratio of:
   c) the number of cells classified as lymphocytes in a plurality of reference samples as defined by a predetermined axial light loss (ALL) limit and a predetermined intermediate angle scatter (IAS) limit; divided by
   d) the number of cells classified as lymphocytes in a plurality of reference samples as defined by a predetermined axial light loss (ALL) limit that is adjacent to the ALL limit in c) and a predetermined intermediate angle scatter (IAS) limit that is adjacent to the IAS limit in c).

11. The method according to claim 1, wherein the value is a lymphocyte DSS value that is based on a depolarized side scatter (DSS) measurement of a distribution of cells in the blood sample that are classified as a lymphocytes, and wherein the reference criterion is based on a DSS distribution and a DSS skew for a plurality of reference samples.

12. The method according to claim 1, wherein the reference criterion is the average rate of decrease in the number of cells in a plurality of reference samples.

13. The method according to claim 1, wherein the reference criterion is the average rate of decrease of the cells that are classified as lymphocytes in a plurality of reference samples.

14. The method according to claim 13, wherein the value includes a measure of variation that would be expected for the value based on a plurality of samples that have been previously analyzed on the same hematology analyzer.

15. The method according to claim 14, wherein the measure of the variation that would be expected from the value is at least one standard deviation of the plurality of samples that have been previously analyzed on the same hematology analyzer.

16. The method according to claim 1, wherein the reference criterion is a number that describes a characteristic of a plurality of reference samples, plus or minus a measure of the variation that would be expected for the number based on a plurality of reference samples that have been previously analyzed on the same hematology analyzer.

17. The method according to claim 16, wherein the measure of the variation that would be expected for the number is at least one standard deviation of the plurality of reference samples that have been previously analyzed on the same hematology analyzer.

18. The method according to claim 1, wherein calculating the difference between each value and a reference criterion comprises calculating a weighted sum of the differences between each of a plurality of values and a plurality of reference criteria.

19. The method according to claim 1, wherein the difference between the value and the reference criterion indicates an increasing rate of decrease in the number of cells classified as lymphocytes in the sample, and wherein the sample is flagged as containing fragile white blood cells.

20. The method according to claim 1, wherein the difference between the value and the reference criterion indicates a decreasing rate of decrease in the number of cells classified as lymphocytes in the sample, and wherein the sample is flagged as containing lysis-resistant red blood cells.

* * * * *